United States Patent
Westenfelder, II et al.

(10) Patent No.: US 11,872,088 B2
(45) Date of Patent: Jan. 16, 2024

(54) PROXIMITY DETECTION FOR A SURGICAL LIGHT

(71) Applicant: American Sterilizer Company, Mentor, OH (US)

(72) Inventors: David A. Westenfelder, II, Mantua, OH (US); Jill A. Sanders, Cleveland, OH (US); Michael Hollopeter, Kirtland, OH (US); Joseph James Groszek, Lakewood, OH (US); David Jesurun, South Euclid, OH (US); Ian Hugh Cook, Pawtucket, RI (US)

(73) Assignee: American Sterilizer Company, Mentor, OH (US)

(*) Notice: Subject to any disclaimer, the term of this patent is extended or adjusted under 35 U.S.C. 154(b) by 0 days.

(21) Appl. No.: 17/152,823

(22) Filed: Jan. 20, 2021

(65) Prior Publication Data
US 2021/0236231 A1 Aug. 5, 2021

Related U.S. Application Data

(60) Provisional application No. 62/968,202, filed on Jan. 31, 2020.

(51) Int. Cl.
*A61B 90/30* (2016.01)

(52) U.S. Cl.
CPC ...... *A61B 90/30* (2016.02); *A61B 2562/0257* (2013.01)

(58) Field of Classification Search
CPC . A61B 90/30; A61B 2562/0257; A61B 90/35; A61B 2017/00738;
(Continued)

(56) References Cited

U.S. PATENT DOCUMENTS 4,884,008 A 11/1989 Bossler et al.
6,880,957 B2 4/2005 Walters
(Continued)

FOREIGN PATENT DOCUMENTS

CN 102 252 216 A 11/2011
EP 1741975 A2 1/2007
(Continued)

OTHER PUBLICATIONS

International Search Report and Written Opinion for corresponding PCT International Application No. PCT/US2021/014062, dated Jul. 1, 2021.
(Continued)

*Primary Examiner* — Tsion Tumebo
(74) *Attorney, Agent, or Firm* — Renner, Otto, Boisselle & Sklar, LLP

(57) ABSTRACT

A surgical light head and proximity detection method includes a housing, a plurality of light emitting elements arranged in the housing and configured to direct light at a target region of interest, and a plurality of distance sensors arranged in the housing. At least two of the distance sensors have field of views that overlap to define a common detection region of interest and the common detection region of interest at least partially overlaps with the target region of interest. The light head may have a plurality of integrally formed tilted seats that position the distance sensors relative to a center line of focus of the surgical light head. The distance sensors may be integrated in the housing via an optical component that is sealed relative to the housing and covers the distance sensor while enabling transmission and receipt of distance sensing signals therethrough.

32 Claims, 16 Drawing Sheets

(58) Field of Classification Search
CPC ...... A61B 2090/061; A61B 2090/0818; F21V 23/0442; F21V 23/0471; G01S 17/88; G01S 17/08; G01S 17/87; F21W 2131/205; F21Y 2115/10; G01C 3/00
See application file for complete search history.

(56) References Cited

U.S. PATENT DOCUMENTS

| | | | |
|---|---|---|---|
| 7,339,684 B2 | 3/2008 | Njolstad | |
| 8,292,804 B2 | 10/2012 | Marka et al. | |
| 9,016,916 B2* | 4/2015 | Marka | F21V 23/04 600/249 |
| 9,119,668 B2 | 9/2015 | Marka et al. | |
| 9,491,835 B2 | 11/2016 | Elfring et al. | |
| 9,559,781 B2 | 1/2017 | Sattler | |
| 9,609,722 B2 | 3/2017 | Law | |
| 9,638,406 B1* | 5/2017 | Liang | F21V 23/0471 |
| 10,240,751 B2 | 3/2019 | Zapata et al. | |
| 10,271,398 B2 | 4/2019 | Hollopeter et al. | |
| 10,363,114 B2 | 7/2019 | Hollopeter et al. | |
| 10,473,312 B2* | 11/2019 | Strölin | A61B 90/30 |
| D882,845 S | 4/2020 | Theodon | |
| D882,846 S | 4/2020 | Theodon | |
| D886,347 S | 6/2020 | Theodon | |
| D888,308 S | 6/2020 | Theodon | |
| 10,670,235 B1* | 6/2020 | Moghal | F21V 23/0442 |
| 2003/0185009 A1* | 10/2003 | Walters | F21V 23/0442 362/802 |
| 2009/0318771 A1* | 12/2009 | Marka | A61B 90/30 362/249.02 |
| 2014/0066722 A1* | 3/2014 | Marka | F21V 23/0442 600/249 |
| 2015/0208478 A1* | 7/2015 | Sattler | A61B 90/30 315/151 |
| 2016/0061396 A1 | 3/2016 | Bosua et al. | |
| 2017/0030573 A1* | 2/2017 | Alexanderson | H05B 47/115 |
| 2017/0296291 A1* | 10/2017 | Bärlund | G09F 19/18 |
| 2018/0116755 A1* | 5/2018 | Hollopeter | G08B 5/36 |
| 2018/0124892 A1* | 5/2018 | Hollopeter | H05B 45/12 |
| 2018/0147020 A1* | 5/2018 | Strölin | A61B 90/30 |
| 2018/0209623 A1 | 7/2018 | Strolin | |
| 2019/0041026 A1* | 2/2019 | Stolte | F21V 3/02 |
| 2019/0041572 A1* | 2/2019 | Dahlen | F21V 3/02 |
| 2019/0141660 A1 | 5/2019 | He et al. | |
| 2019/0203920 A1 | 7/2019 | Strolin | |
| 2020/0248898 A1* | 8/2020 | Chen | F21V 23/0464 |
| 2020/0337797 A1* | 10/2020 | Hollopeter | H05B 47/175 |

FOREIGN PATENT DOCUMENTS

| | | |
|---|---|---|
| EP | 3056164 A1 | 8/2016 |
| JP | 1611207 S | 8/2018 |

OTHER PUBLICATIONS

Invitation to Pay Additional Fees and Partial Search Report for corresponding PCT International Application No. PCT/US2021/014062, dated Apr. 28, 2021.

Written Opinion of the International Preliminary Examining Authority (WO/IPEA) for corresponding PCT International Application No. PCT/US2021/014062, dated Jan. 27, 2022.

* cited by examiner

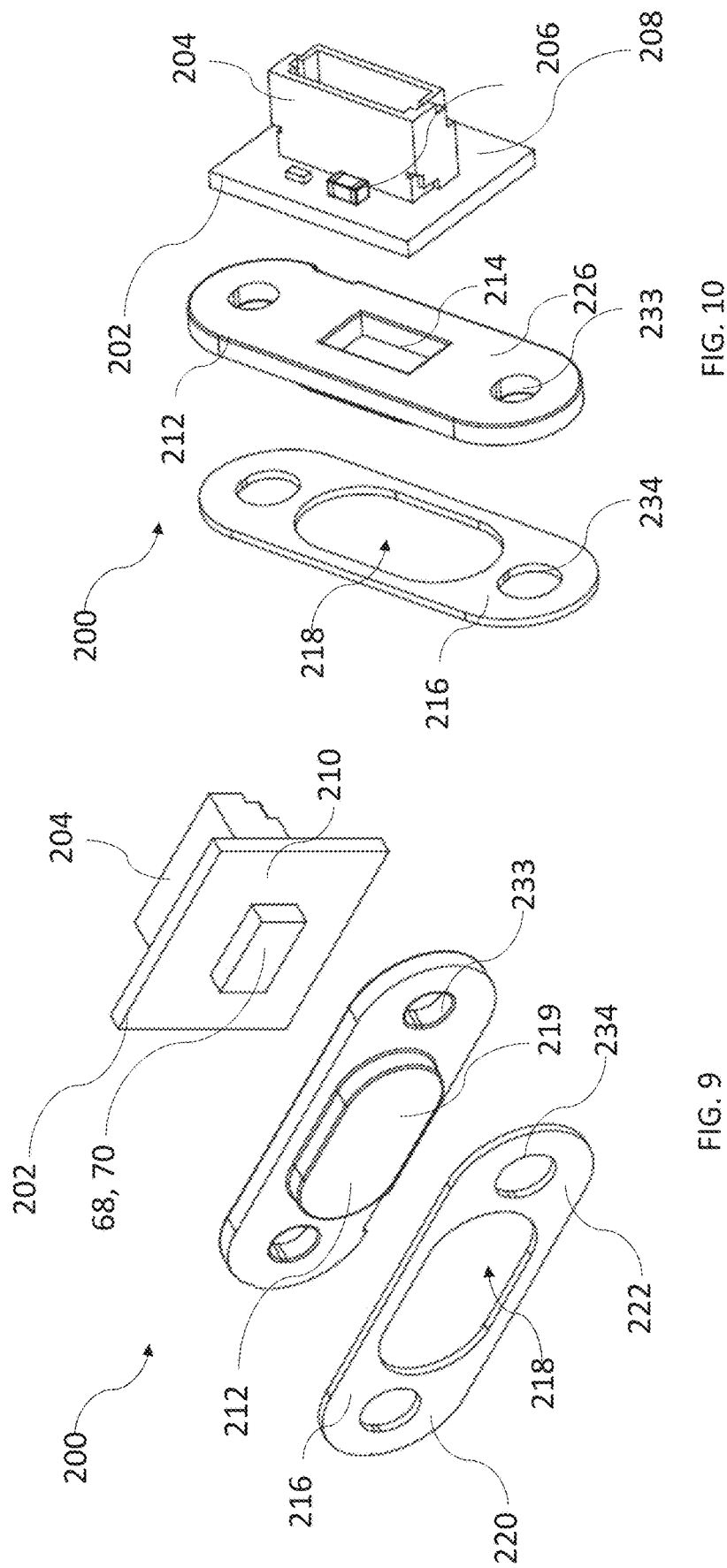

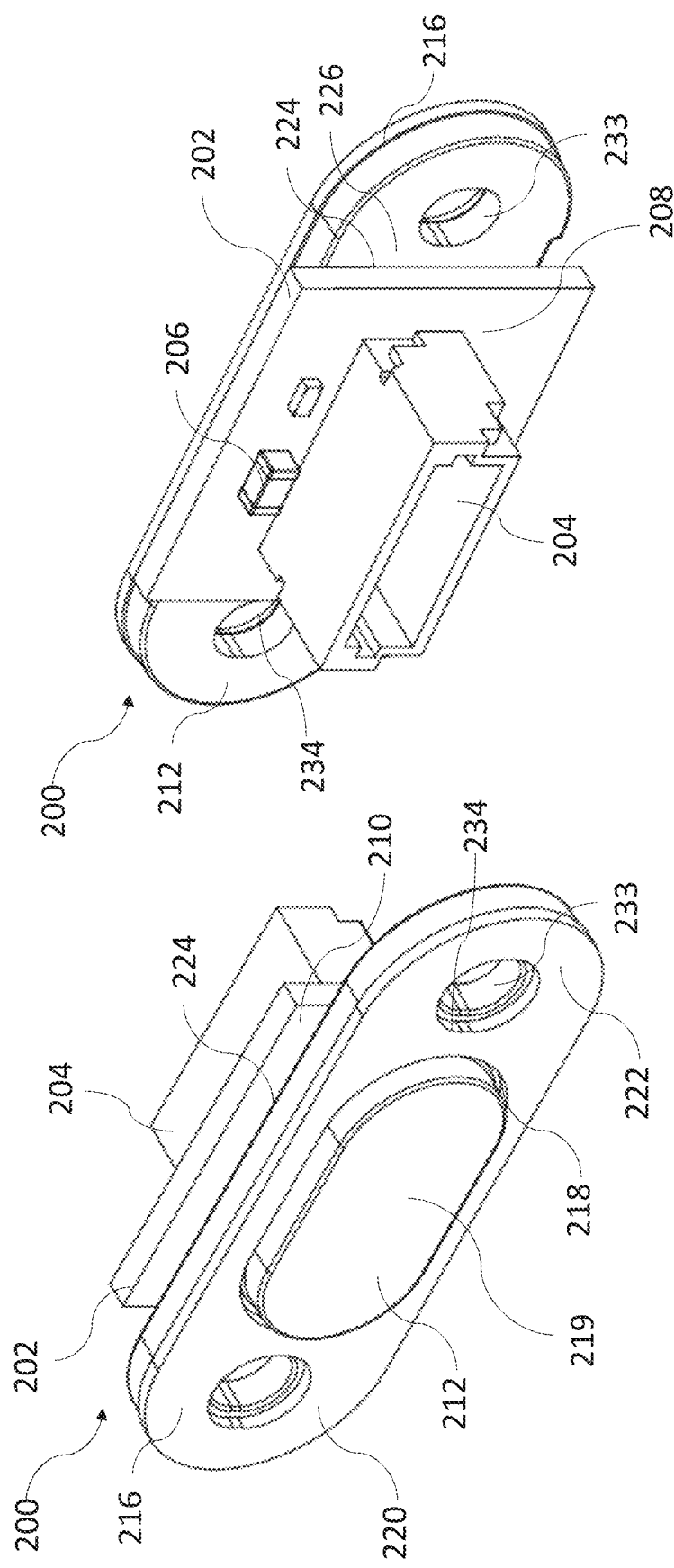

PROXIMITY DETECTION FOR A SURGICAL LIGHT

This application claims priority to U.S. Patent Application No. 62/968,202 filed Jan. 31, 2020, the entire disclosure of which is hereby incorporated by reference.

FIELD OF INVENTION

This application relates generally to a surgical light, and more particularly to a system and method for aiming and controlling a light output and proximity detection of surgical lights.

BACKGROUND

Surgical lights are used in operating rooms to provide increased light to a specific area of the room. For example, the surgical light may be positioned in an operating room and configured to provide increased light to a specific area of a surgical patient. The light may include a light housing containing a light source and a distance sensor that measures a distance from the light housing to the object to be illuminated, such that attributes of the light emitted from the light housing may be altered based on the distance detected by the distance sensor. However, conventional sensor systems may be susceptible to blockage that results in inaccurate measurements. For example, a head of a surgeon or other medical professional may block the sensor and consequently cause inaccurate distance measurements.

SUMMARY OF INVENTION

According to one aspect of the invention, a surgical light head includes a housing, a plurality of light emitting elements arranged in the housing and configured to direct light at a target region of interest, and a plurality of distance sensors arranged in the housing. At least two of the distance sensors have field of views that overlap to define a common detection region of interest, wherein the common detection region of interest at least partially overlaps with the target region of interest.

Embodiments of the invention may include one or more of the following additional features separately or in combination.

The plurality of distance sensors may be mounted along a periphery of the housing in a spaced relationship relative to each other.

The plurality of distance sensors may be evenly spaced.

The plurality of distance sensors may be obliquely angled relative to a center line of focus of the surgical light head.

The plurality of distance sensors may be obliquely angled relative to the center line of focus by an angle that is between 0.5 and 20 degrees.

The plurality of distance sensors may include a single inner distance sensor arranged proximate the center line of focus and a plurality of outer distance sensors that are radially spaced relative to the inner distance sensor.

The surgical light head may further include an annular shape first lens that has a rotation axis, wherein the housing includes a housing cover including a cavity within which the annular shape first lens is rotatable about the rotation axis, wherein the housing cover includes a second lens, and wherein the outer distance sensors are arranged radially outwardly relative to the annular shape first lens and the second lens.

The field of views may be defined by cones having an opening angle that is between 5 and 40 degrees.

The plurality of distance sensors may include between five and ten distance sensors that are separate and spaced about the housing.

The housing may define a plurality of seats configured for supporting the plurality of distance sensors. The seats may be obliquely angled toward a center line of focus of the surgical light head.

The plurality of seats may be molded with the housing as a single monolithic component.

The plurality of seats may include a single inner seat formed proximate the center line of focus and a plurality of outer seats that are formed on a periphery of the housing and radially spaced from the inner seat.

The surgical light head may include a plurality of distance sensor assemblies that each include a corresponding one of the plurality of distance sensors and a printed circuit board assembly including an electrical interface communicatively coupled between the housing and the corresponding one of the plurality of distance sensors.

Each of the plurality of distance sensor assemblies may include an optical component that covers the corresponding one of the plurality of distance sensors. The optical component may be sealed to the housing and coupled to the printed circuit board assembly. The corresponding one of the plurality of distance sensors may be configured to transmit and receive distance sensing signals through the optical component.

The surgical light head may include an adhesive layer disposed between the optical component and the housing.

The printed circuit board assembly and the optical component may be adhered by an acrylate adhesive material.

The distance sensor and the optical component may define an air gap therebetween.

The surgical light head may include a plurality of locating posts formed on the housing that are engageable with the optical component.

The plurality of locating posts may be integrally formed with the housing as a single monolithic component.

The locating posts may have a tapered shape.

The plurality of distance sensors may be infrared distance sensors.

According to another aspect of the invention, a surgical light head includes a housing defining a center line of focus of the surgical light head, a plurality of distance sensors, and a plurality of tilted seats formed on the housing and configured for supporting the plurality of distance sensors. The plurality of tilted seats are obliquely angled toward the center line of focus.

The plurality of tilted seats may be molded with the housing as a single monolithic component.

The plurality of tilted seats may include a single inner seat formed proximate the center line of focus and a plurality of outer seats that are formed on a periphery of the housing and radially spaced from the inner seat.

The surgical light head may include an annular shape first lens that has a rotation axis. The housing may include a housing cover including a cavity within which the annular shape first lens is rotatable about the rotation axis, wherein the housing cover includes a second lens, and the outer seats may be arranged radially outwardly relative to the annular shape first lens and the second lens.

The plurality of tilted seats may be obliquely angled relative to the center line of focus by an angle that is between 0.5 and 20 degrees.

The surgical light head may include a plurality of distance sensor assemblies that each include a corresponding one of the plurality of distance sensors and a printed circuit board assembly including an electrical interface communicatively coupled between the housing and the corresponding one of the plurality of distance sensors.

Each of the plurality of distance sensor assemblies may include an optical component that covers the corresponding one of the plurality of distance sensors. The optical component may be matingly engageable against a corresponding one of the tilted seats and coupled to the printed circuit board assembly and the corresponding one of the plurality of distance sensors may be configured to transmit and receive distance sensing signals through the optical component.

The surgical light head may include an adhesive layer disposed between the optical component and the corresponding one of the tilted seats.

The printed circuit board assembly and the optical component may be adhered by an acrylate adhesive material.

The distance sensor and the optical component may define an air gap therebetween.

The surgical light head may include a plurality of locating posts that are formed on the plurality of tilted seats and engageable with a corresponding one of the plurality of distance sensor assemblies.

The plurality of locating posts may be integrally formed with the housing as a single monolithic component.

The locating posts may protrude from a corresponding one of the plurality of tilted seats and have a tapered shape that tapers in a protrusion direction away from the corresponding one of the plurality of tilted seats.

The plurality of distance sensors may be infrared distance sensors.

The surgical light head may include a plurality of light emitting elements arranged in the housing and configured to direct light at a target region of interest that defines the center line of focus. The plurality of distance sensors may be obliquely angled toward the center line of focus when seated in the tilted seats, whereby at least two of the distance sensors have field of views that overlap to define a common detection region of interest. The common detection region of interest may at least partially overlap with the target region of interest.

The plurality of distance sensors may be mounted along a periphery of the housing in a spaced relationship relative to each other.

The plurality of distance sensors may be evenly spaced.

The plurality of distance sensors may include a single inner distance sensor and a plurality of outer distance sensors that are radially spaced relative to the inner distance sensor.

The field of views may be defined by cones having an opening angle that is between 5 and 40 degrees.

The plurality of distance sensors may include between five and ten distance sensors that are separate and spaced about the housing.

According to another aspect of the invention, a surgical light head includes a housing, and a plurality of distance sensor assemblies integrated into the housing. Each of the plurality of distance sensor assemblies includes a distance sensor, a printed circuit board assembly having an electrical interface communicatively coupled between the housing and the distance sensor, and an optical component that covers the distance sensor, with the optical component being sealed to the housing and coupled to the printed circuit board assembly. The distance sensor is configured to transmit and receive distance sensing signals through the optical component.

The surgical light head may include an adhesive layer disposed between the optical component and the housing.

The printed circuit board assembly and the optical component may be adhered by an acrylate adhesive material.

The distance sensor and the optical component may define an air gap therebetween.

The housing may define a plurality of tilted seats configured for supporting the plurality of distance sensor assemblies, with the tilted seats being obliquely angled toward a center line of focus of the surgical light head.

The plurality of tilted seats may be molded with the housing as a single monolithic component.

The plurality of tilted seats may include a single inner seat formed proximate the center line of focus and a plurality of outer seats that are formed on a periphery of the housing and radially spaced from the inner seat.

The surgical light head may include a plurality of locating posts formed on the tilted seats that are engageable with the optical component.

The locating posts may protrude from a corresponding one of the plurality of tilted seats and have a tapered shape that tapers in a protrusion direction away from the corresponding one of the plurality of tilted seats.

The surgical light head may include a plurality of light emitting elements arranged in the housing and configured to direct light at a target region of interest, with at least two of the distance sensor assemblies having field of views that overlap to define a common detection region of interest. The common detection region of interest may at least partially overlaps with the target region of interest.

The plurality of distance sensor assemblies may be mounted along a periphery of the housing in a spaced relationship relative to each other.

The surgical light head may include an annular shape first lens that has a rotation axis, with the housing including a housing cover including a cavity within which the annular shape first lens is rotatable about the rotation axis. The housing cover may include a second lens, and the outer distance sensor assemblies may be arranged radially outwardly relative to the annular shape first lens and the second lens.

The plurality of distance sensor assemblies may be evenly spaced.

The plurality of distance sensor assemblies may be obliquely angled relative to a center line of focus of the surgical light head.

The plurality of distance sensor assemblies may be obliquely angled relative to the center line of focus by an angle that is between 0.5 and 20 degrees.

The plurality of distance sensor assemblies may include a single distance sensor assembly arranged proximate the center line of focus and a plurality of outer distance sensor assemblies that are radially spaced relative to the inner distance sensor assembly.

The field of views may be defined by cones having an opening angle that is between 5 and 40 degrees.

The plurality of distance sensor assemblies may include between five and ten distance sensor assemblies that are separate and spaced about the housing.

According to another aspect of the invention, a method of proximity detecting for a surgical light head includes arranging a plurality of light emitting elements in a housing to direct light at a target region of interest, and arranging at least two distance sensors to have field of views that overlap to define a common detection region of interest. The common detection region of interest at least partially overlaps with the target region of interest.

Arranging the at least two distance sensors may include angling the at least two distance sensors toward a center line of focus of the surgical light head.

According to another aspect of the invention, a method of forming a surgical light head includes arranging a plurality of light emitting elements in a housing, spacing a plurality of distance sensors along a periphery of the housing, and orienting the plurality of distance sensors to be obliquely angled toward a center line of focus of the surgical light head.

The method may include molding a housing having a plurality of tilted seats as a single monolithic component, with the plurality of tilted seats being obliquely angled toward the center line of focus, and arranging the plurality of distance sensors against the plurality of tilted seats to position the plurality of distance sensors.

The method may include communicatively coupling the housing and one of the plurality of distance sensors with a printed circuit board assembly, mounting the printed circuit board assembly to an optical component, covering the distance sensor with the optical component, with the distance sensor being configured to transmit and receive distance sensing signals through the optical component, and sealing the optical component relative to the housing.

The method may include molding locating posts with the housing as a single monolithic component and engaging the optical component with the locating posts.

The method may include using a heat staking process to secure the optical component to the housing.

The method may include defining an air gap between the distance sensor and the optical component.

The following description and the annexed drawings set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the invention.

FIG. 9 is an exploded perspective view of a distance sensor assembly that includes a distance sensor and an optical component.

FIG. 10 is another exploded perspective view of the distance sensor assembly.

FIG. 11 is a front perspective view of the assembled distance sensor assembly.

FIG. 12 is a rear perspective view of the assembled distance sensor assembly.

DETAILED DESCRIPTION

Figure 1:
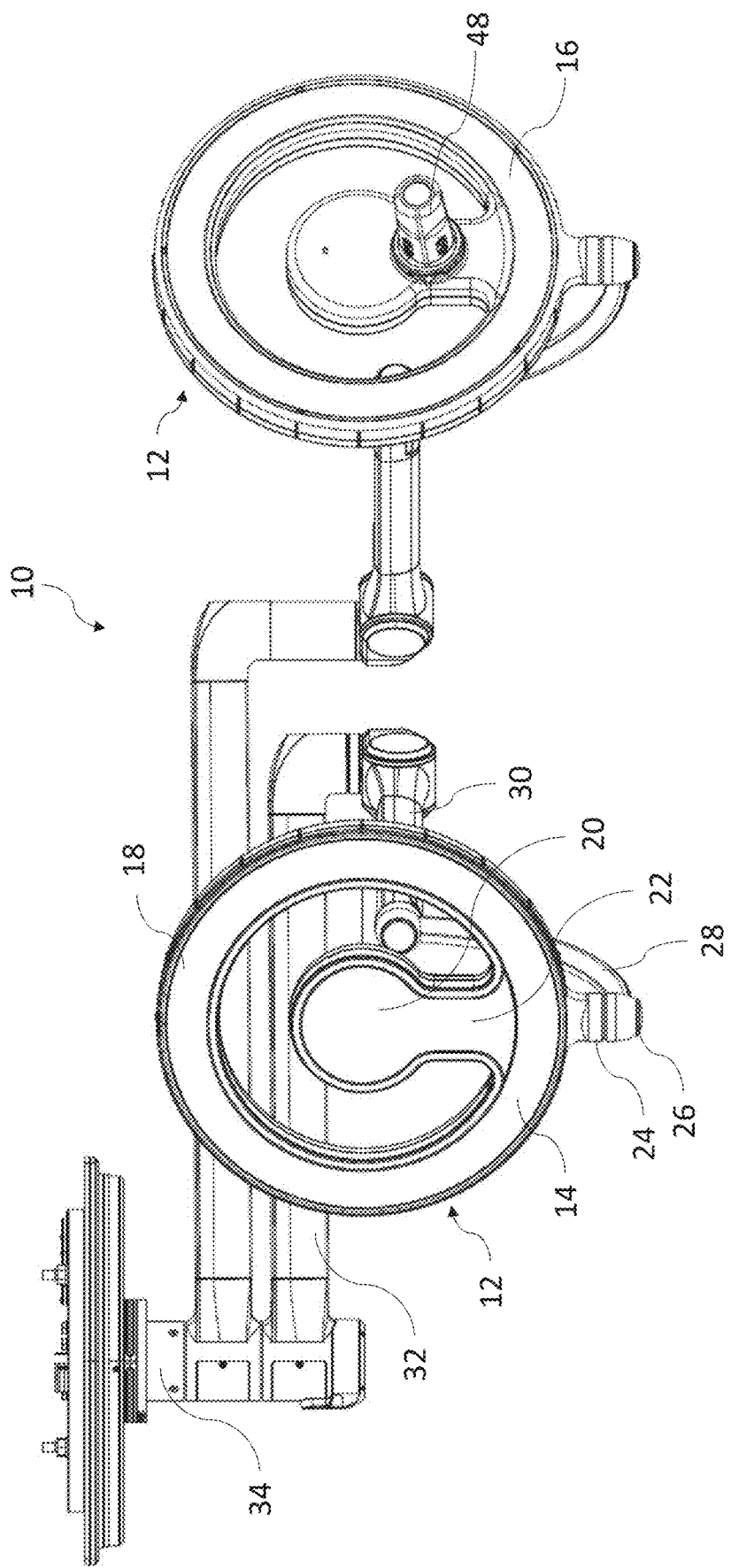
FIG. 1 is a side elevation view of an overall configuration of a medical device support system in accordance with an embodiment of the invention, showing a top of a left positioned light head and a bottom a right positioned light head.

While the present invention can take many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications of the described embodiments, and any further applications of the principles of the invention as described herein, are contemplated as would normally occur to one skilled in the art to which the invention relates.

The present application is directed to a proximity detection system and method that may be suitable for use in various applications. An exemplary application includes surgical lights such as those used in operating rooms to provide increased light to a specific area of the room. For example, the proximity detection system may be implemented in a light head structure of the surgical light. Still other suitable applications include transportation applications, such as in vehicles, or more particularly, in self-driving vehicles, and home automation applications. For example, the proximity detection system described herein may be used for motion sensing in a room of a home.

The proximity detection system and method according to the present application includes an arrangement of distance sensors, such as infrared distance sensors, to determine blockage of light from a main light source, such that the system can adjust the light being emitted to ensure that a target of illumination is adequately illuminated. In an exemplary application, blockage may be caused by the head of a medical personnel in an operating room or other medical equipment. The arrangement of distance sensors includes at least two distance sensors that have a spaced relationship and are configured to have overlapping field-of-views (FOVs) that define a common detection region of interest. The common detection region of interest at least partially overlaps with a target region of interest that is illuminated by the light source.

Each of the distance sensors may have a tilted orientation. For example, in a surgical light head, the distance sensor may be tilted relative to a center line of focus of the light head rather than facing in a straight downward direction, i.e. in a direction parallel to the center line of focus, such as in conventional light heads in which the FOVs of the sensors are non-overlapping and thus susceptible to blockage that impedes accurate distance measurements. In an exemplary embodiment, the housing cover may be formed to have an integral tilted seat for supporting the distance sensor in the tilted orientation such that the precise positioning of the distance sensors is accommodated by the shape of the light head itself. In an exemplary embodiment, the distance sensors may also be integrated into the light head using optical components that are sealed relative to the light head.

Using the proximity detection system and method described herein is advantageous in that the system is configured for aiming each distance sensor at a light focal point to ensure the measured distance represents the distance to the target of illumination. Arranging the distance sensors to be separated and in spaced locations along the light head, such as along the periphery of the light head, ensures that the detected distance to the target is not sensitive to blockage of one or several sensors due to the arrangement of all of the sensors. Integrating the distance sensors into the light head is further advantageous in providing ingress protection for the light head without sacrificing accuracy of the distance sensors.

Figure 2:
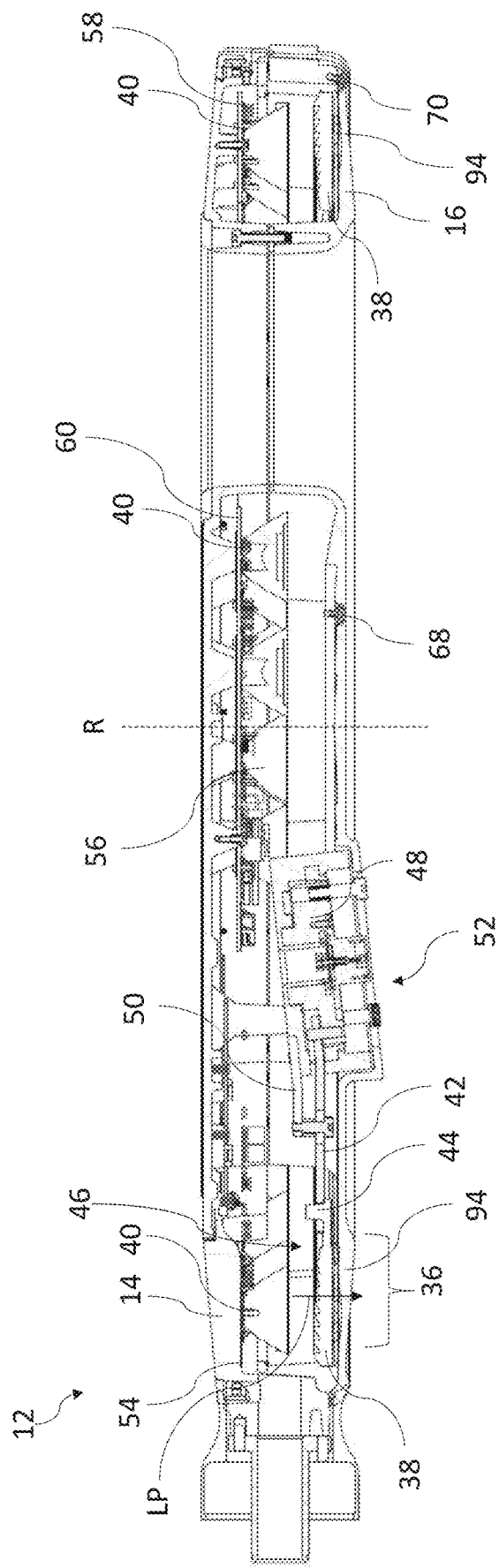
FIG. 2 is a side cross section view of a light head in accordance with an embodiment of the invention, showing a housing base, a housing cover, and internal components of the light head.

FIGS. 1 and 2 show an exemplary medical device support system 10 in which the proximity detection system may be implemented. The medical device support system 10 includes two light heads 12 in accordance with an embodiment of the invention. As shown in FIG. 1, each light head 12 of the system 10 includes a housing base 14 and a housing cover 16 that together define an overall form and structure of the light head 12. Each light head 12 includes an annular shape outer portion 18, an inner round portion 20, and a radially protruding arm 22 that connects the annular shape outer portion 18 to the inner round portion 20. The housing base 14 and the housing cover 16 may be formed of metal, thermoplastic, or thermoset materials, or combinations of these materials. Other materials may be suitable.

The light head 12 may be configured to be repositioned using a load balancing arm and yoke assembly. In an exemplary embodiment, a bushing or other coupling member 24 is provided on each light head 12 for rotatably connecting the respective light head 12 to a distal arm 26 of a yoke assembly 28. The yoke assembly 28 is arranged on a distal end of a load balancing arm 30 and is configured to support the respective light head 12 for multi-axis movement relative to the load balancing arm 30. The medical device support system 10 may include two load balancing arms 30, one for each light head 12, and each load balancing arm 30 may be pivotably mounted to a distal end of an extension arm 32. The extension arm 32 is mounted to a central shaft or support column 34 that is suspended from the ceiling, or mounted to a wall or stand. The extension arm 32 is configured for rotational movement about the shaft 34. Using the load balancing arms 30 and the yoke assemblies 28 is advantageous in enabling positioning of the light heads 12 to a proper orientation relative to, for example, a patient operating table and healthcare professionals in the operating room.

Referring in addition to FIG. 2, the housing cover 16 includes a housing lens 36 and each light head 12 further includes an annular shape lens 38, a plurality of light emitting elements 40, and a motion transfer member 42. The housing lens 36 and the annular shape lens 38 are arranged in a light emitting path LP of the plurality of light emitting elements 40. The motion transfer member 42 may include a lever, gear arrangement, or articulating assembly and is configured to movably interact with a boss 44 of the annular shape lens 38 to rotate the annular shape lens 38 about a rotational axis R within an interior cavity 46 of the housing cover 16.

As shown in FIG. 1, a driving source 48, such as a handle of the light head 12 may be movably coupled with the motion transfer member 42, such that motion from the driving source 48 translates into rotation of the annular shape lens 38 about the rotational axis R. For example, the annular shape lens 38 may be rotated to adjust the distribution of light from the light head 12. As shown in FIG. 2, movement of the driving source 48 is transferred to the annular shape lens 38 via a lever 50 and a motion transfer assembly 52. The motion occurs within a low overall height structure which is advantageous for maneuverability of the light head 12 and enabling a structure that has improved laminar flow conditions.

As shown in FIG. 2, an inside surface 54 of the housing base 14 supports the plurality of light emitting elements 40, which may be for example light emitting diodes (LEDs) or any other suitable light source. In the illustrative embodiment, a plurality of collimators 56 are also mounted to the inside surface 54 of the housing base 14 and in the light emitting paths LP of the respective plurality of light emitting elements 40. The collimators 56 collect and direct, and/or collimate, the light into narrow beams. In one form, the collimators 56 may comprise total internal reflection (TIR) lenses. The light emitting elements 40, the collimators 56, the annular shape lens 38, and the housing lens 36 may have an axial arrangement where axial refers to the direction of emission of light from the light heads 12, or downward in FIG. 2.

Figure 3:
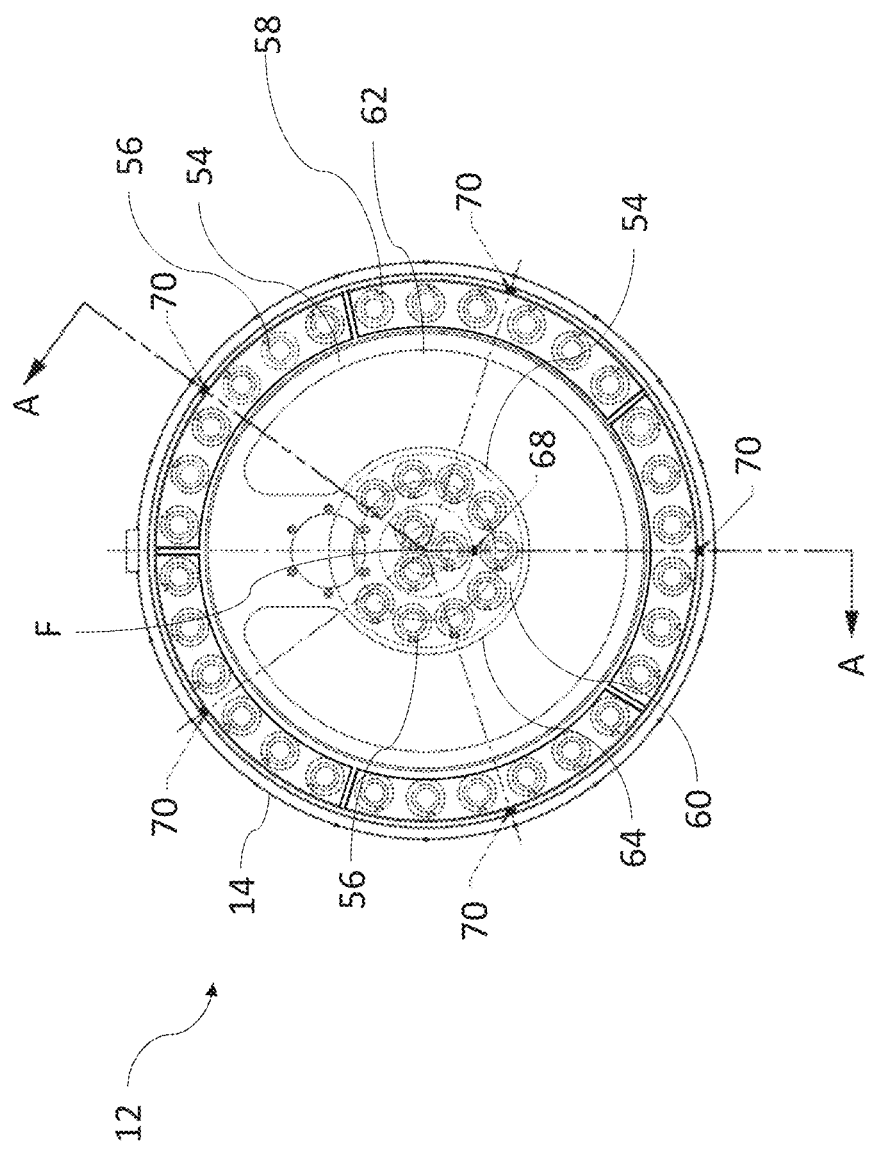
FIG. 3 is a bottom plan view of the housing base, a plurality of collimators, and a plurality of distance sensors.

Referring in addition to FIG. 3, the light emitting elements 40 and the collimators 56 may be grouped together in modules 58, 60. The modules 58, 60 may be mounted to the inside surface 54 of the housing base 14. Some of the modules 60 may be arc shape and mounted to the inside surface 54 of an annular shape outer base portion 62 of the housing base 14 that corresponds to the annular shape outer portion 18 of the light head 12. One round module 60 may be mounted to the inside surface 54 of an inner round base portion 64 of the housing base 14 that corresponds to the inner round portion 20 of the light head 12.

In the illustrative embodiment, five arc shape modules 58 are mounted to the inside surface 54 of the annular shape outer base portion 62 and one round module 60 is mounted to the inside surface 54 of the inner round base portion 64. Each of the five arc shape modules 58 may have six light emitting elements 40 (shown in FIG. 2) and collimators 56, and the round inner module 60 may have 12 light emitting elements 40 and collimators 56. The light emitting elements 40 and the collimators 56 in the five arc shape modules 58 may be evenly distributed about the annular shape outer base portion 62. The round inner module 60 may include an outer ring of nine light emitting elements 40 and collimators 56 and a triangle of three within the outer ring. Any suitable fasteners, risers, and bosses may be used to secure the modules 58, 60 to the inside surface 54 of the housing base 14.

Further details of an exemplary surgical light system suitable for the present application are described in U.S. Provisional Application No. 62/968,196 filed Jan. 31, 2020, and titled "Lighthead with Rotating Lens Assembly and Method of Operating Same," which is attached herewith, and which is incorporated by reference for all purposes as if fully set forth herein.

Figure 4:
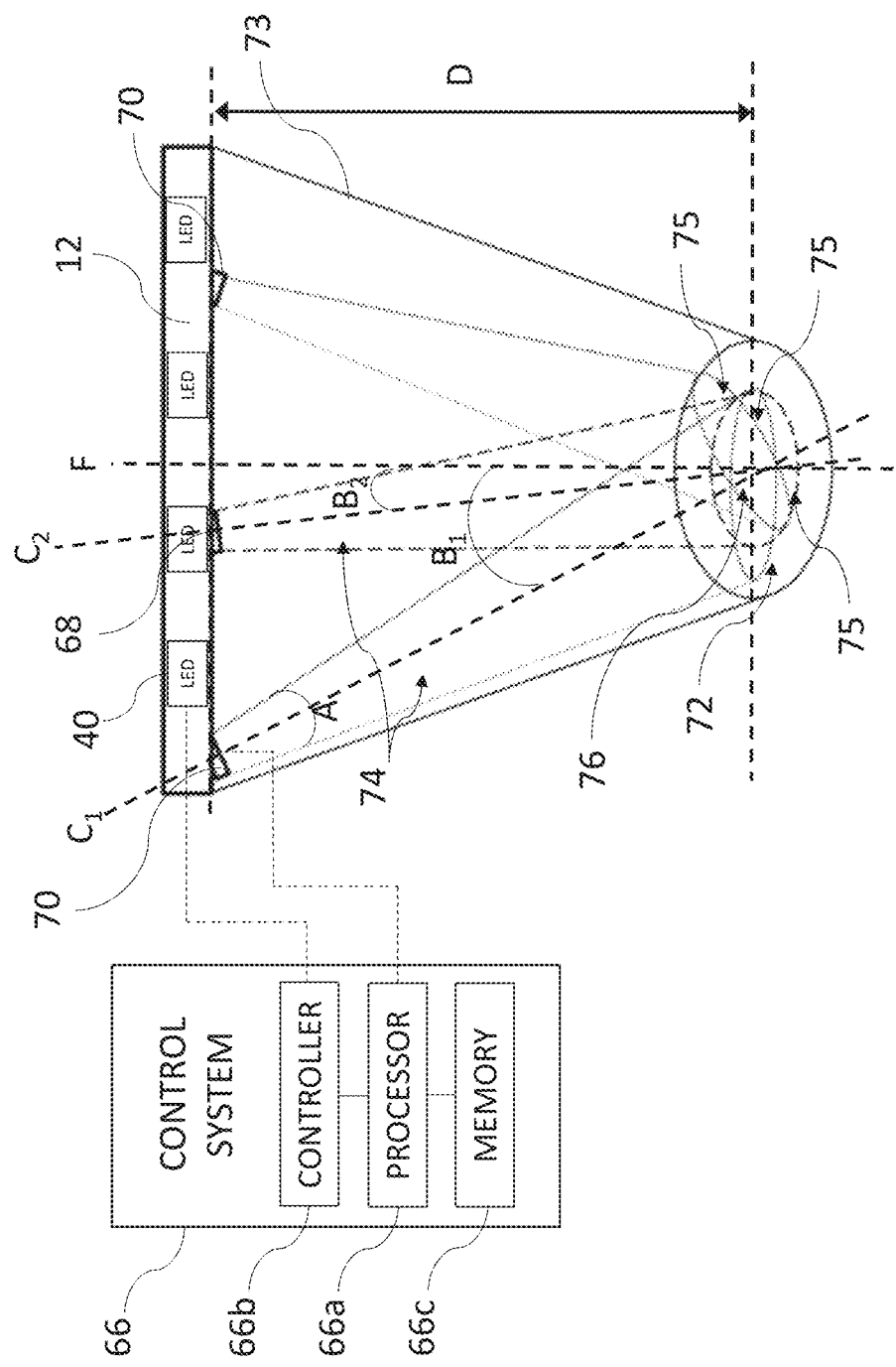
FIG. 4 shows a region of interest of the light head, fields of view of the distance sensors, and a control system for controlling the light head based on measurements of the distance sensors.

Referring in addition to FIG. 4, each light head 12 is communicatively coupled with a control system 66 which includes control elements integrated into the light head housing, handle, or support structure. The control system 66 may include a main processor 66a including any suitable microprocessor, control processing unit (CPU), control circuitry, or the like. A controller 66b may be communicatively coupled between the processor 66a and components in the light head 12 for adjusting the components based on instructions received from the processor 66a. For example, the controller 66b may be configured to adjust an intensity of the light emitting elements 40. Further details of an exemplary surgical light with power balancing system suitable for the present application are described in U.S. Provisional Application No. 62/968,208 filed Jan. 31, 2020, and titled "Surgical Light Head with Beam Spreading and Adjustable Power Balancing," which is attached herewith, and which is incorporated by reference for all purposes as if fully set forth herein.

A memory 66c may also be provided as part of the control system 66. The memory 66c may contain stored data pertaining to operation of the light head 12 that is used by the processor 66a in providing instructions to the controller 66b. For example, the memory 66c may be configured to store data pertaining to a default light intensity for the light emitting elements 40 or a look-up table having data pertaining to position or light intensity adjustments that correspond to particular blockages. Further details of an exemplary surgical light and system for identification of illumination abnormalities and automatic compensation suitable for the present application are described in U.S. Provisional application Ser. No. 16/393,168 filed Apr. 24, 2019, and titled "System and Method for Identification of Illumination Abnormalities and Automatic Compensation Therefor," which is attached herewith, and which is incorporated by reference for all purposes as if fully set forth herein.

The control system 66 further includes a plurality of proximity or distance sensors or detectors 68, 70, which may also be referred to as sensors, proximity sensors, optical transceivers, or optical emitters, that are integrated into the light head 12 (shown in FIGS. 2 and 3). The plurality of distance sensors 68, 70 are in communication with the processor 66a (shown in FIG. 4) and are configured to provide readings representing the distance between the distance sensors 68, 70 and incident light on an object such as a patient, surgical equipment, or a physician's head or hand, to the processor 66a. The plurality of distance sensors 68, 70 are arranged in the housing cover 16 of the light head 12 and are configured to detect the distance to the object, where the distance sensor 68, 70 has within a field of view (FOV) of the distance sensor 68, 70 a target region of interest 72 that is a distance D from the distance sensors 68, 70. The control system 66 is configured to control the lighting of the light head 12 based on at least in part the detected data received from the distance sensors 68, 70. In exemplary applications, the processor 66a may be configured to determine an average of all of the measurements received from the distance sensors 68, 70.

The target region of interest 72 may include a specific target, such as a patient on a surgical table. A target may be defined as an area which the user intends to illuminate by aiming the light 73 produced by the surgical light. The target region of interest 72 may be defined as the area that is illuminated by the light head 12 which is typically at a distance of one meter from the light head 12. "Target" "region of interest," "target region", and "target region of interest," etc. may be used with reference to the same area. The target region of interest 72 is formed by the light emitting elements 40 that emit light and the lenses 36, 38, 56 that aim, redirect, spread, converge, and or focus the light. A center line of focus F of the light head 12 is defined by a central axis of the target region of interest 72 that is formed by the illumination, i.e. an axis extending through the point at which the light beam converges or focuses. The center line of focus F may be the same as or proximate the rotational axis R of the annular shape lens 38 (shown in FIG. 2) and the center line of focus F may be directly centered in the light head 12 or slightly offset depending on the geometry of the light head 12 and the positioning and aiming of the light emitting elements 40 and the positioning and adjusting capabilities of the lenses 36, 38, 56.

The distance sensors 68, 70 may include any suitable sensor type. For example, the distance sensors 68, 70 may use visible light, infrared light, ultrasonic waves or any other known output for measuring the distance D from the light head 12 to the target. In an exemplary embodiment, the distance D may be approximately one meter. Each distance sensor 68, 70 has a field of view (FOV) 74 that extends outwardly from the corresponding distance sensor 68, 70 and defines a detection region of interest 75 for the corresponding distance sensor 68, 70. The FOV 74 may be defined as the area that is seen when looking outwardly from the point along the light head 12 where the distance sensor 68, 70 is located, whereas the detection region of interest 75 for the distance sensor 68, 70 may be defined as the area from which the distance sensor makes measurements. Each distance sensor 68, 70 may be oriented such that the corresponding detection region of interest 75 is aimed at the focal point of the light emitted from the light head 12.

While the individual surgical light beams are converging, the FOV 74 of each distance sensor 68, 70 is increasing. Each distance sensor 68, 70 is oriented at an oblique angle relative to the center line of focus F such that each FOV 74 is slanted or tilted relative to the center line of focus F. The FOV 74 of each distance sensor 68, 70 may define a cone of sensitivity or a frustoconical shape that is radially increasing starting from where the corresponding distance sensor 68, 70 is mounted to the light head 12. The frustoconical shape may define a central axis $C_1$, $C_2$ and have an opening angle A that is between 5 and 40 degrees. The opening angle A may be approximately 20 degrees. Each FOV 74 may have the same opening angle or a different opening angle.

The distance sensors 68, 70 have slanted or tilted orientation such that the FOVs 74 of at least two of the distance sensors 68, 70 overlap at the detection region of interest 75 to define a common FOV area and thus a common detection region of interest 76. The common detection region of interest 76 of the distance sensors 68, 70 at least partially overlaps with the target region of interest 72. The distance sensors 68, 70 may include at least one inner distance sensor 68 that is arranged proximate the center line of focus F and a plurality of outer distance sensors 70 that are radially spaced relative to the inner distance sensor 68. The plurality of distance sensors 68, 70 may be obliquely angled relative to the center line of focus F. In an exemplary embodiment, an angle $B_1$ between the central axis $C_1$ of the FOV 74 of the outer distance sensor 70 and the center line of focus F may be between 10 and 20 degrees. In the illustrative embodiment, the angle $B_1$ is approximately 16.5 degrees. The other outer distance sensors 70 may have the same angle $B_1$ or different angles. The angle $B_2$ between the central axis $C_2$ of the FOV 74 of the inner distance sensor 68 and the center line of focus F may be less than the angle $B_1$, such as between 0.5 degrees and 10 degrees. In the illustrative embodiment, the angle $B_2$ is approximately three degrees. Accordingly, the FOV 74 of the inner distance sensor 68 extends more nearly parallel relative to the center line of focus F as compared with the FOV 74 of the outer distance sensor 70.

As shown in FIG. 3, the plurality of distance sensors 68, 70 may include only a single inner distance sensor 68 and a plurality of outer distance sensors 70 that are spaced radially outwardly relative to the single distance sensor 68. The distance sensors 68, 70 may be integrated into the housing cover 16 (shown in FIG. 1). The plurality of outer distance sensors 70 are arranged along a periphery, in the illustrative embodiment a circumference, of the housing cover 16 in a spaced relationship relative to each other such that all of the distance sensors 68, 70 are spaced and separated relative to each other. The single inner distance sensor 68 may be arranged radially offset relative to the center line of focus F. The plurality of outer distance sensors 70 may be radially spaced from the center line of focus F by a same distance, and spaced relative to each other by a same distance. The outer distance sensors 70 may be arranged radially outwardly relative to the light emitting elements 40 and the collimators 56 when the housing cover 16 is engaged with the housing base 14. Further, the outer distance sensors 70 may be arranged radially outwardly relative to the housing lens 36 and the annular shape lens 38.

Any number of distance sensors 68, 70 may be used. Between five and ten distance sensors 68, 70 may be used. The distance sensors 68, 70 may be separate and spaced about the housing 14, 16. For example, as shown in FIG. 3, six distance sensors 68, 70 may be used including five outer distance sensors 70 that are evenly spaced by approximately 72 degrees. Using six distance sensors 68, 70 is advantageous in that blockage of between one and three detectors, for example by a surgeon's body or surgical tools, does not adversely impact the readings of the remaining detectors. For example, the processor 66a may use a voting algorithm that ignores the blocked detection measurement and the resulting averaged distance is unaffected. Other arrangements of the distance sensors 68, 70 may be suitable. For example, the distance sensors 70 may have a non-uniform or uneven distribution about the housing cover 16 of the light head 12.

Figure 5A:
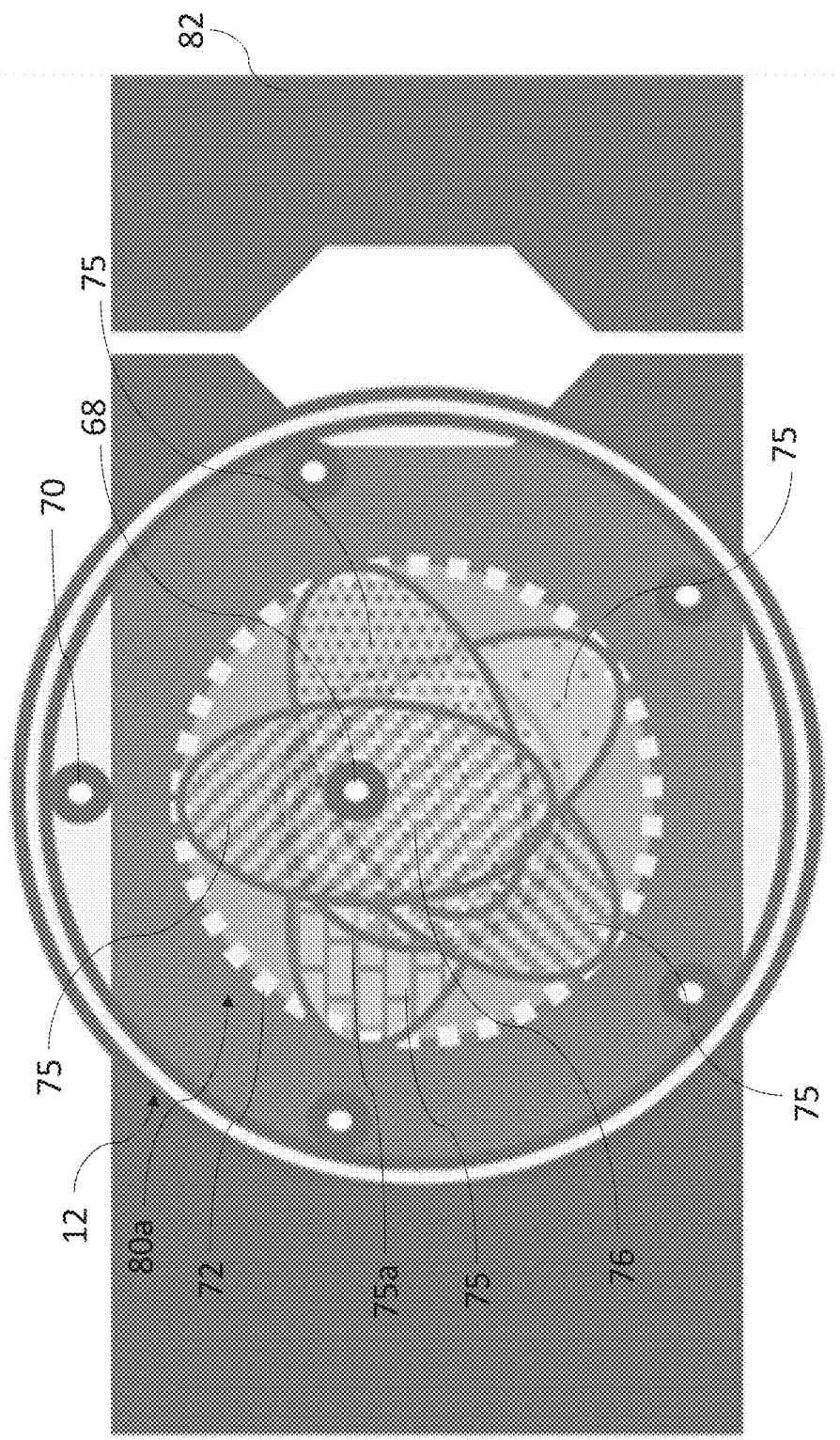
FIG. 5A shows a detection pattern provided by the plurality of distance sensors.
Figure 5C:
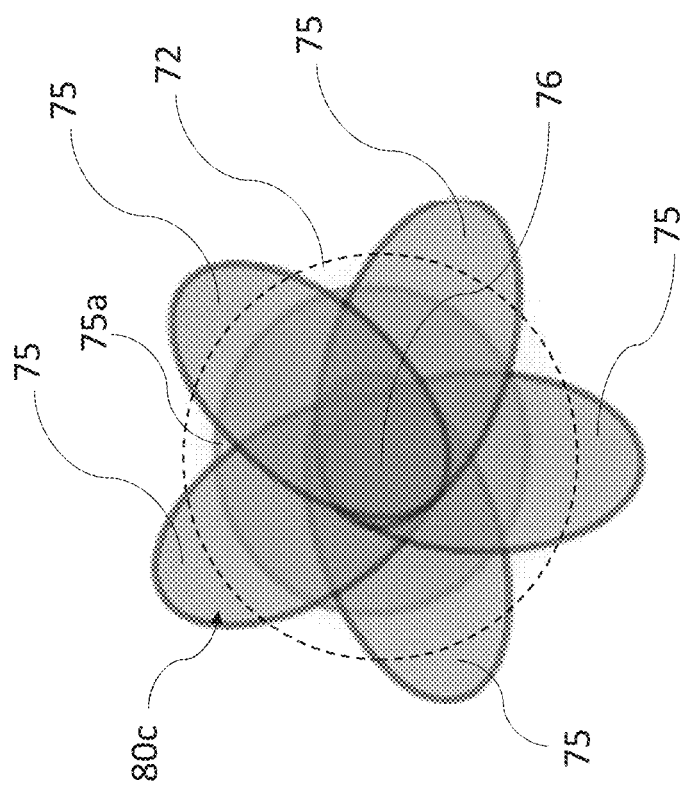
FIG. 5C shows a detection pattern provided by the plurality of distance sensors when the distance sensors are farther from the target than in FIG. 5A.
Figure 5B:
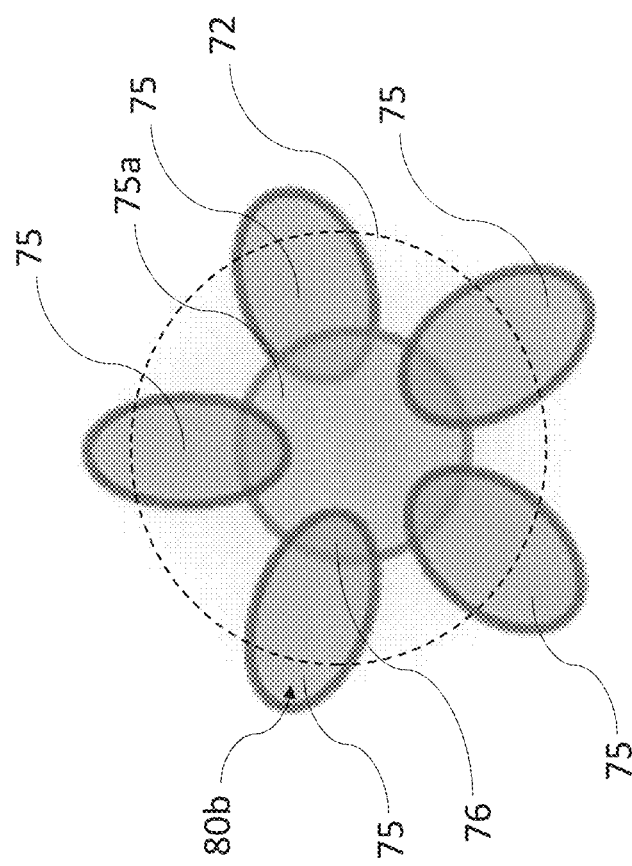
FIG. 5B shows a detection pattern provided by the plurality of distance sensors when the distance sensors are closer to the target than in FIG. 5A.

FIGS. 5A-5C show a detection region pattern 80a, 80b, 80c provided by the arrangement of the distance sensors 68, 70 of FIG. 3 relative to a surgical table 82. FIG. 5A shows the detection region pattern 80a when the distance sensors 68, 70 are oriented such that the distance D between the distance sensors 68, 70 and the target is approximately one meter. The light head 12 is configured to provide the converging light that defines the target region of interest 72 for illumination and each distance sensor 68, 70 is configured to have a corresponding detection region of interest 75, as defined by the FOV 74 (shown in FIG. 4), that overlaps with the target region of interest 72 of illumination. More than two detection regions of interest 75 may overlap with each other and the detection region of interest 75 (shown as 75a in FIGS. 5A-5C) of the single inner distance sensor 68 arranged proximate the center line of focus F may overlap with all of the detection regions of interest 75 of the outer distance sensors 70.

FIG. 5B shows the detection region pattern 80b when the distance sensors 68, 70 are arranged at a distance D that is less than one meter relative to the target. As shown in FIG. 5B, the region of interest 75a of the single inner distance sensor 68 still overlaps with each of the detection regions of interest 75 of the outer distance sensors 70 such that the target region of interest 72 is overlapped by at least two detection regions of interest 75, 75a. FIG. 5C shows the detection region pattern 80c when the distance sensors 68, 70 are arranged at a distance D that is greater than one meter relative to the target. FIG. 5C shows the regions of interest 75, 75a overlapping with the target region of interest 72.

As shown in FIGS. 5A-5C, the target region of interest 72 and the detection regions of interest 75 may have different shapes and the shapes may be dependent on the distance D between the light head 12 and the target. For example, the target region of interest 72 for illumination may be circular and the detection regions of interest 75 for the distance sensors 68, 70, as defined by the FOVs, may be elliptical as illustrated or oval or circular in shape. The detection region of interest 75 (shown as 75a in FIGS. 5A-5C) for the inner distance sensor 68 may be circular as illustrated or elliptical or oval in shape. The distance sensors 68, 70 may be oriented such that the detection regions of interest 75 converge at approximately one meter from the light head (for example perpendicularly downward in FIG. 4), such that all the regions maximally overlap at the region of interest 72, for example, at a one meter distance. Other patterns may be provided and the patterns may be altered by altering the orientation and spacing of the distance sensors 68, 70. In exemplary embodiments, the distance sensors 68, 70 may be co-located with, or located proximate to the modules 58, 60 of the light emitting elements 40 at predetermined locations along the periphery of the housing cover 16 to further ensure maximum overlap and that readings are received from the target. The distance sensors 68, 70 may be located in the middle of the modules 58, 60. For example, as illustrated, the distance sensor 70 may be arranged between two sets of three light emitting elements 40. Arranging the distance sensors 68, 70 proximate the modules 58, 60 enables control of the modules 58, 60 in a one to one ratio with the detected blockage.

Figure 6:
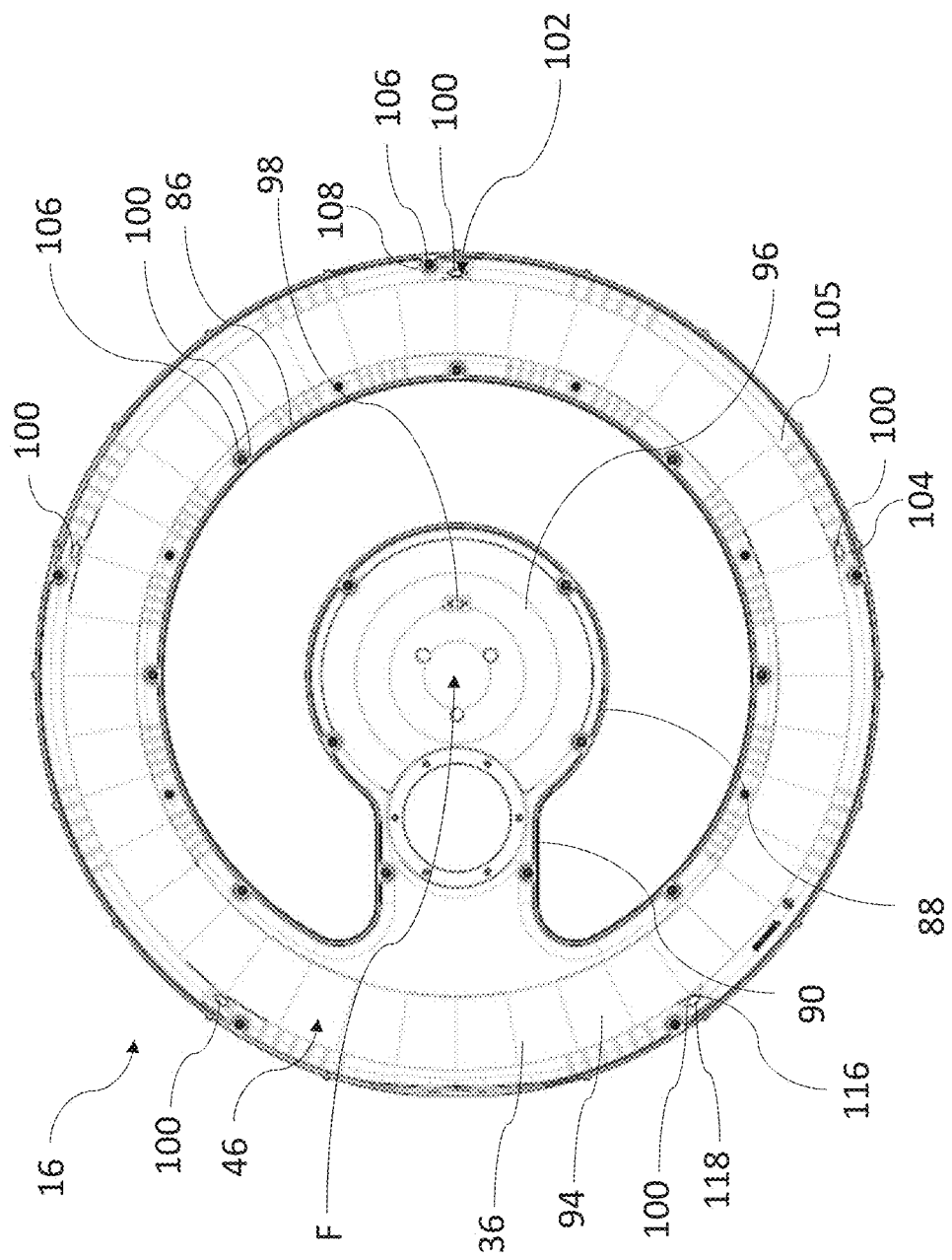
FIG. 6 is a top plan view of a housing cover including tilted seats for supporting the plurality of distance sensors.

Referring now to FIG. 6, each distance sensor may be integrated into the housing cover 16 of the light head via support features that are integrally formed in the housing cover 16. In an exemplary embodiment of the housing cover 16, the housing cover 16 may be formed as a single monolithic component and include an annular shape outer cover 86 and an inner round cover 88 that are connected by an arm cover 90 extending radially therebetween. The radially extending arm cover 90 may also arrange the annular shape outer cover 86 and the inner round cover 88 in concentric relation to one another, and/or in concentric relation to the rotational axis R of the annular shape lens 38 (shown in FIG. 2). The housing cover 16 defines the interior cavity 46 which has three interconnected portions corresponding to the annular shape outer cover 86, the inner round cover 88, and the arm cover 90 extending radially therebetween.

The housing cover 16 also includes the housing lens 36 which includes an annular shape outer lens 94 and an inner round lens 96. The annular shape outer lens 94 forms a bottom surface of the annular shape outer cover 86 and the inner round lens 96 forms a bottom surface of the inner round cover 88. In an alternate form, the bottom wall of the annular shape outer cover 86 and/or the inner round cover 88 may be formed by a transparent non-lens material, i.e. a non-light bending material, and the annular shape outer lens 94 and/or the inner round lens 96 may be positioned, for example, above the transparent non-lens bottom walls and secured to surrounding structure of the housing cover 16.

The annular shape outer lens 94 and the inner round lens 96 are arranged in the light emitting paths LP of the plurality of light emitting elements 40 (shown in FIG. 2). The annular shape lens 38 (shown in FIG. 2) is positioned between the annular shape outer lens 94 and the light emitting elements 40 in the light emitting path LP. The collimators 56 (shown in FIG. 2) are also arranged in the light emitting paths LP of the plurality of light emitting elements 40 in the annular shape outer portion 18 (shown in FIG. 1) of the light head 12 positioned between the light emitting elements 40 and the annular shape lens 38, and in the inner round portion of the light head 12 positioned between the light emitting elements 40 and the inner round lens 96. The annular shape lens 38 and the housing lens 36, and the collimators 56 if provided, can take on any form for spreading and/or bending the light emitted by the light emitting elements 40.

The distance sensors 68, 70 operate in conjunction with the light emitting elements 40 and lenses 36, 38, 56 and are integrated into the housing cover 16 via tilted seats 98, 100 that are slanted or tilted and formed in the housing cover 16. The tilted seats 98, 100 are configured to support the distance sensors 68, 70 (shown in FIGS. 3-5) and position the distance sensors 68, 70 relative to the light emitting elements 40 and lenses 36, 38, 56. The distance sensors 68, 70 may be obliquely angled toward the center line of focus F when seated in the tilted seats 98, 100, whereby at least two of the distance sensors 68, 70 have field of views that overlap to define the common detection region of interest 76. The tilted seats 98, 100 may be formed by a planar surface that defines a through-going aperture 102, such that a corresponding distance sensor 68, 70 is engageable against the planar surface and faces outwardly through the aperture 102 for performing detection. The apertures 102 of the tilted seats 98, 100 may have any suitable shape and the shape may correspond to a shape of the distance sensor. For example, the apertures 102 may be circular, elliptical, or oval in shape.

The tilted seats 98, 100 are formed to be slanted or tilted relative to the center line of focus F of the light head 12 (shown in FIG. 4), which may also be the center of the annular shape lens 38. The outer tilted seats 100 may be arranged radially outwardly relative to the rotatable annular shape lens 38 and the housing cover annular shape outer lens 94. The tilted seats 98, 100 are tilted such that when the distance sensors 68, 70 are seated against or in contacting engagement with the tilted seats 98, 100, the distance sensors 68, 70 provide the desired overlapping FOVs 74 (shown in FIG. 4). Each tilted seat 98, 100 may be tilted radially inwardly toward the center line of focus F, for example, to be obliquely angled toward the center line of focus F. The tilted seats 98, 100 may be obliquely angled relative to the center line of focus F by an angle that is between 0.5 and 20 degrees, for example. The pattern and number of tilted seats 98, 100 corresponds to the pattern and number of distance sensors 68, 70. For example, one tilted inner seat 98 may be arranged proximate the center line of focus F for receiving the inner distance sensor 68 and a plurality of tilted outer seats 100 may be arranged to receive the plurality of outer distance sensors 70. The tilted outer seats 100 may be equally spaced along the periphery of the housing cover 16, and the tilted outer seats 100 may be radially spaced from the inner seat 98. In exemplary embodiments, more tilted seats 98, 100 may be provided than distance sensors 68, 70 to provide flexibility in patterns and/or locations of the distance sensors 68, 70. Any empty seats 98, 100 may be plugged to prevent contaminants from entering the housing of the light head 12. The tilted seats 98, 100 may be defined within a recessed portion 104 of the housing cover 16 that is recessed relative to an outer peripheral surface 105 formed in the housing cover 16. Accordingly, the distance sensor 68, 70 is accommodated against the tilted seat 98, 100 within the recessed portion 104 without interfering with other components in the housing cover 16.

The housing cover 16 may further include threaded openings 106 that are formed in bosses 108 of the housing cover 16. The bosses 108 are circumferentially arranged and spaced and are configured to receive fasteners for connecting the housing base 14 and the housing cover 16 (shown in FIG. 1). A plurality of the bosses 108 are formed on the outer peripheral surface 105 in the annular shape outer cover 86 of the housing cover 16. Some of the bosses 108 may be formed adjacent the recessed portions 104 and the tilted seats 98, 100. Both the tilted seats 98, 100 and the bosses 108 may be molded or formed integrally with the housing cover 16 as a single monolithic component.

Figure 7:
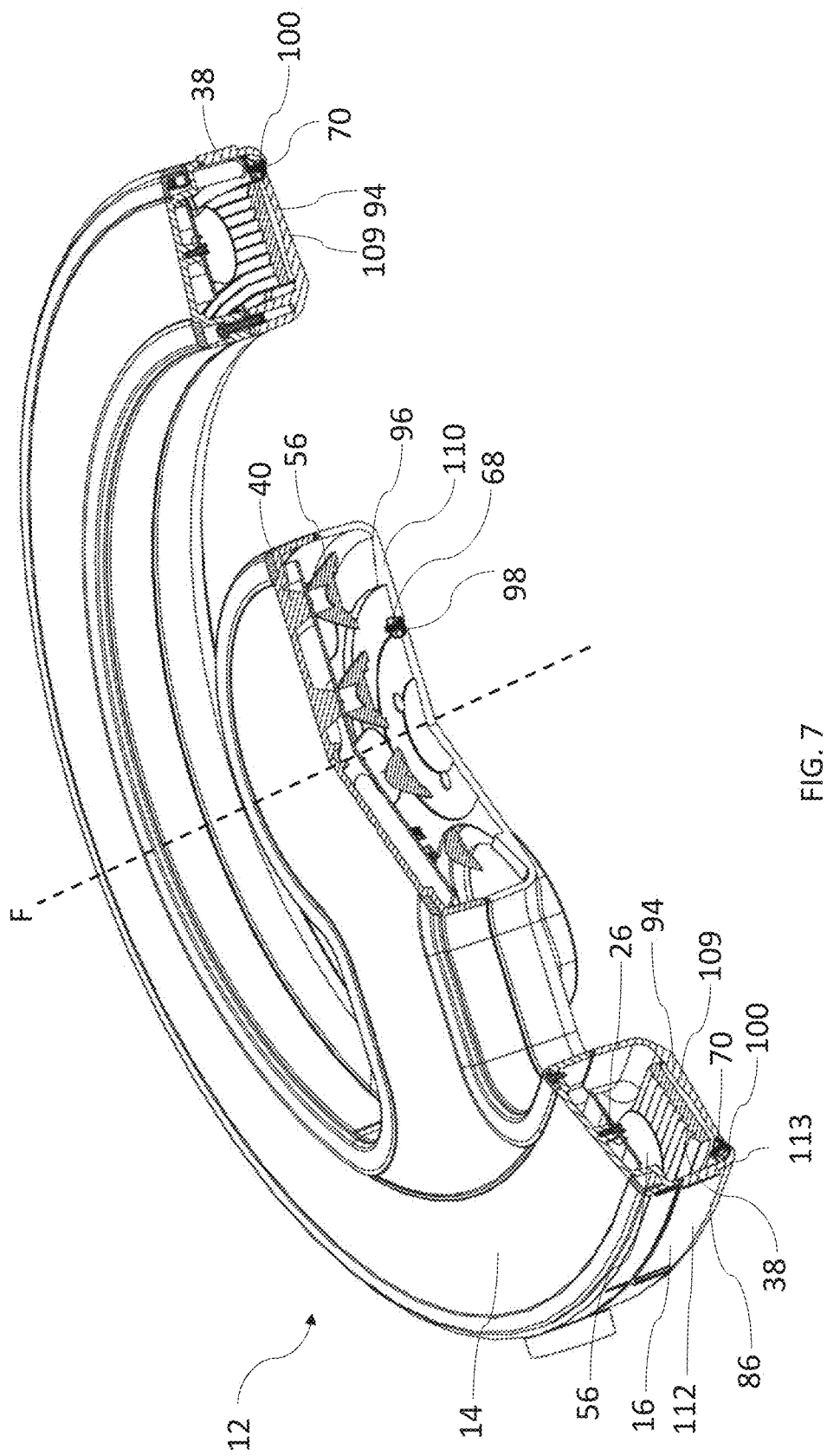
FIG. 7 is a perspective cross section view of the light head as cut along line A-A of FIG. 3.
Figure 8:
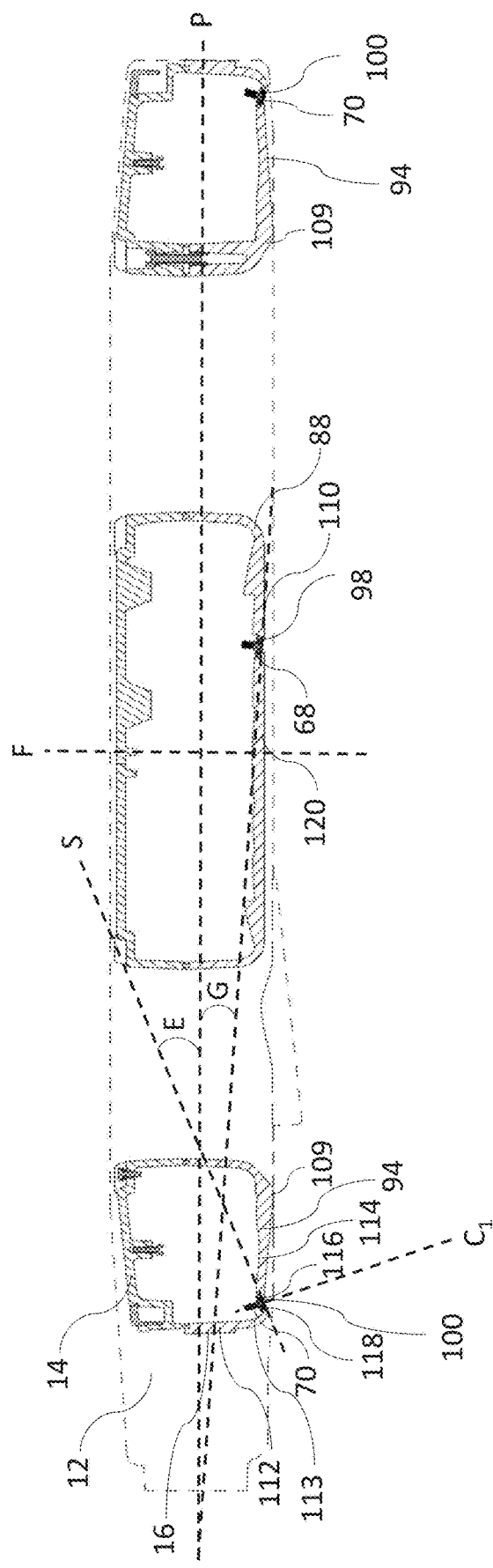
FIG. 8 is a side cross section view of the light head showing the tilted seats and the distance sensors arranged in the tilted seats.

FIGS. 7 and 8 show further details of the tilted seats 98, 100 formed in the housing cover 16 with the distance sensors 68, 70 being seated in the tilted seats 98, 100. FIG. 7 is a cross-sectional view of the light head 12 shown in FIG. 3 as cut along line A-A. The bottom of the recessed portions 104 that define the tilted seats 98, 100 are formed by the bottom surfaces of the housing cover 16. The annular shape outer lens 94 forms a bottom wall 109 of the annular shape outer cover 86 and the inner round lens 96 forms a bottom wall 110 of the inner round cover 88. The bottom walls 109, 110 define the tilted seats 98, 100 and their respective apertures 102. As shown in FIG. 7, the tilted seats 98, 100 may be positioned below the annular shape lens 38 which, in turn, is positioned below the collimators 56 and the light emitting elements 40 supported by the housing base 14. The annular shape lens 38 is positioned between the collimators 56 and the bottom wall 109 in which the tilted seat 100 is formed. As also shown in FIG. 7, the annular shape lens 38 may have a top surface that is formed as a stepped surface that bends individual portions of the light beams. For example, the annular shape lens 38 may have a plurality of Fresnel wedges.

With further reference to FIG. 8, the tilted outer seats 100 are formed at a radially outer portion of the bottom wall 109. The bottom wall 109 is continuous with a side wall 112 of the housing cover 16 that extends upright relative to the bottom wall 109 for engagement with the housing base 14. The tilted seat 100 is arranged proximate a curved wall 113 connecting the bottom wall 109 and the side wall 112. The bottom wall 109 and the side wall 112 may each be formed to have a non-uniform contour. For example, as shown in FIG. 8, the bottom wall 109 may be formed to have a bottom surface 114 that extends radially outwardly and upwardly toward the tilted seat 100 to define a radially inner edge 116 of the tilted seat 100. The curved wall 113 may curve radially inwardly and upwardly toward the tilted seat 100 to define a radially outer edge 118 of the tilted seat 100 that is lower relative to the radially inner edge 116, but parallel with the radially inner edge 116, thus forming the angle of the seat 100 for the distance sensor 70. The inner and outer edges 116, 118 are also shown in FIG. 6 and are formed in the recessed portion 104.

The radially inner and outer edges 116, 118 of the tilted seat 100 define the aperture 102 that receives the distance sensor 70 such that the distance sensor 70 includes an engaging surface that engages the perimeter of the aperture 102. The aperture 102 may be formed to have a dimension suitable to receive different types of distance sensors. The tilted seat 100 is formed to define a seating plane S which is defined as a plane within which the detecting face of the distance sensor 70 extends or the plane along which the distance sensor 70 contacts the tilted seat 100. The seating plane S is normal to the central axis $C_1$ of the distance sensor 70 (as also shown in FIG. 4).

The seating plane S is tilted by an oblique angle E relative to a plane P in which the light head 12 extends, with the plane P being normal to the center line of focus F of the light head 12. The angle E may be between 10 and 20 degrees, and in exemplary embodiments, the angle E may be approximately 16.5 degrees. Many different angles are suitable. When the distance sensor 70 is seated, meaning that the body of the distance sensor 70 rests against the tilted seat 100, the distance sensor 70 is angled radially inwardly to ensure that the detection region of interest of the distance sensor 70 overlaps with the target region of interest (shown in FIG. 4).

Each tilted seat 100 corresponding to the outer distance sensors 70 may have the same shape and may be angled radially inwardly at a same angle relative to the plane P of the light head 12 and the center line of focus F. In other exemplary embodiments, the tilted seats 100 may be formed to have different angles such that each outer distance sensor 70 is oriented differently. The tilted seat 98 corresponding to the inner distance sensor 68 may be formed to have an angle G relative to the plane P that is smaller than the angle E between the seating plane S of the tilted seat 100 and the plane P. The angle G of the tilted seat 98 may be less than 10 degrees such that the inner distance sensor 68 is arranged more nearly parallel with the plane P of the light head 12 as compared with the outer distance sensor 70.

The bottom wall 110 of the inner round cover 88 is formed to define a bottom surface of the tilted seat 98 that receives the inner distance sensor 68. The bottom wall 110 may have a planar bottom surface 120. The angle of the tilted seat 98 may be formed by a tilted surface formed in the recessed portion 104 (shown in FIG. 6) against which the distance sensor 68 is seated.

The tilted seats 98, 100 may be formed to have many different angles and position the distance sensors 68, 70 in different orientations. Forming the tilted seats 98, 100 with the housing cover 16 as a monolithic component is advantageous in that the positioning of the distance sensors 68, 70 is ensured in forming the housing cover 16 and the light head 12 is formed to arrange and aim the distance sensors 68, 70 without impeding the emitted light. In other exemplary embodiments, the distance sensors 68, 70 may be mounted and angled by brackets or other separate attachment mechanisms, including clamps, pins, screws, bolts, adhesives, or any other suitable device. Thus, the housing cover 16 may be formed without the tilted seats 98, 100.

Figure 14:
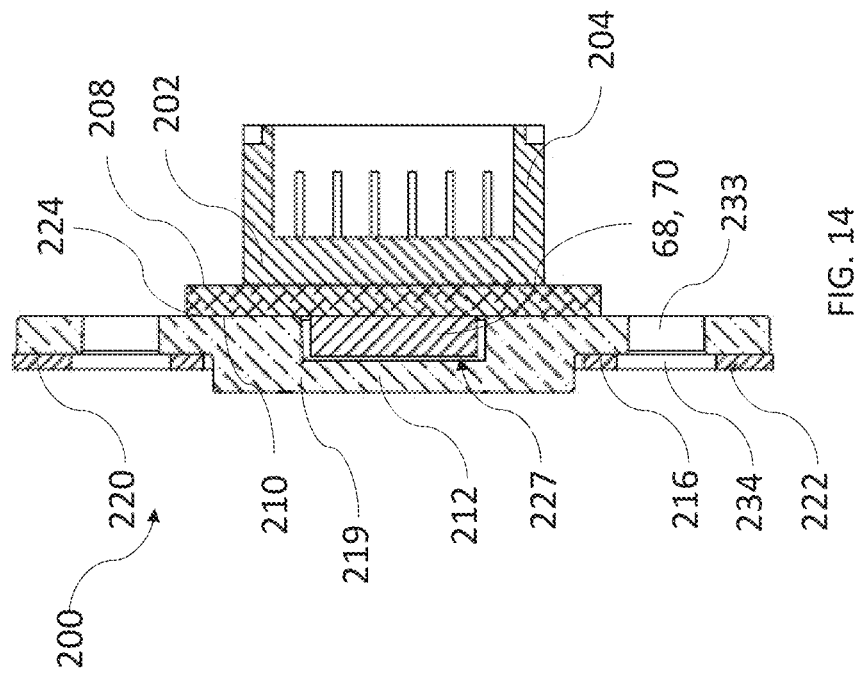
FIG. 14 is a side cross section view of the assembled distance sensor assembly as cut along line B-B of FIG. 13.
Figure 13:
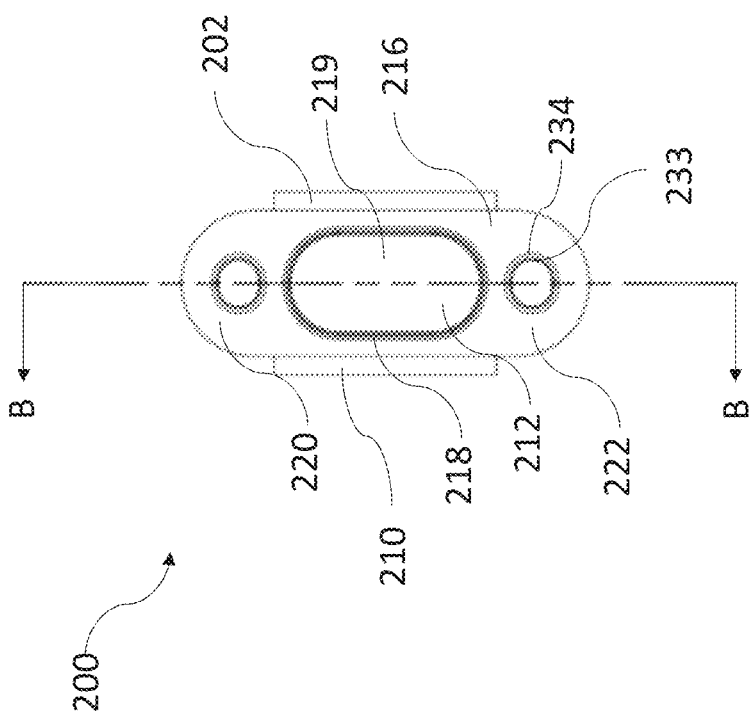
FIG. 13 is a front plan view of the assembled distance sensor assembly.

Referring now to FIGS. 9-14, each distance sensor 68, 70 may be arranged in a distance sensor assembly 200 such that any distance sensor 68, 70 previously shown may be a distance sensor assembly 200. For example, the light head may include six distance sensor assemblies 200 in place of the distance sensors 68, 70 shown in FIG. 3. FIGS. 9 and 10 show exploded views of the distance sensor assembly 200, FIGS. 11 and 12 show the distance sensor assembly 200 as assembled, FIG. 13 shows a front view of the distance sensor assembly 200, and FIG. 14 shows a cross-sectional view of the distance sensor assembly 200 as cut along line B-B in FIG. 13. The distance sensor assembly 200 is configured to be implemented in the light head 12 (shown in FIGS. 7 and 8) and may be configured to be obliquely angled relative to the center line of focus F and obliquely angled relative to the plane P in which the light head 12 extends as previously described (shown in FIG. 8). A plurality of distance sensor assemblies 200 may correspond to a same number of tilted seats 98, 100. Each distance sensor assembly 200 is arranged in a corresponding tilted seat 98, 100, or, in other embodiments, separately mounted to the light head.

The distance sensor assembly 200 includes a printed circuit board assembly (PCBA) 202 that has an electrical interface 204, such as a plug, the distance sensor 68, 70, and associated electronics 206. The electrical interface 204 is disposed on a first surface 208 of the PCBA 202 and extends outwardly from the first surface 208. The distance sensor 68, 70 is disposed on a second surface 210 of the PCBA 202 that opposes the first surface 208. The electrical interface 204 is configured to provide power and communication to the distance sensor 68, 70 from a power source and communication line of the medical device support system 10 (shown in FIG. 1). In an exemplary embodiment, the distance sensor 68, 70 may be an infrared distance sensor, but other sensors may be suitable.

The distance sensor assembly 200 may further include an optical component 212 that is configured for aiming, orienting, and protecting the distance sensor 68, 70. The optical component 212 may be configured to be matingly engageable against a corresponding one of the tilted seats 98, 100 and coupled to the printed circuit board assembly 202. The optical component 212 may be arranged to cover the distance sensor 68, 70 adjacent the second surface 210 of the PCBA 202 and is also configured to be sealed relative to the light head housing, such as the housing cover. As best shown in FIG. 10, a complementary recess 214 may be formed in the optical component 212 to receive and support the distance sensor 68, 70. As described in greater detail below, the distance sensor 68, 70 of the distance sensor assembly 200 may be configured to transmit and receive distance sensing signals through the optical component 212. The optical component 212 may be configured to enable passage of infrared light and block visible light. In other embodiments, the optical component 212 may enable passage and/or blockage of other electromagnetic or ultrasonic waves.

In addition to filtering out undesired light, such as visible light that may interfere with the detection capabilities of the distance sensor 68, 70, the optical component 212 is also advantageous in providing ingress protection for the housing cover 16 by preventing contaminants from entering into the housing cover 16. The optical component 212 may be sealed relative to the light head 12, such as relative to the housing cover 16 (shown in FIG. 7), by any suitable adhesive layer 216. The adhesive layer 216 may be disposed between the optical component 212 and the housing 14, 16. For example, the adhesive layer 216 may be disposed between the optical component 212 and a corresponding one of the tilted seats 98, 100. Thus, the adhesive layer 216 provides an interface between the distance sensor assembly 200 and the housing cover 16. The adhesive layer 216 may be formed as a thin tape material and may have a thickness that is less than a thickness of the optical component 212. An acrylic adhesive material may be suitable. Double-sided foam tapes formed of acrylic adhesive material may be suitable. Still other adhesives may be suitable.

An opening 218 is formed in the adhesive layer 216 to enable the optical component 212 to protrude through the adhesive layer 216. In an exemplary embodiment, a protruding portion 219 of the optical component 212 may have a shape that is complimentary to the aperture 102 formed by the corresponding tilted seat 98, 100 (shown in FIG. 6) such that the optical component 212 is configured for matingly engaging with a perimeter of the aperture 102. In some embodiments, the mating engagement between the optical component 212 and the perimeter of the aperture 102 may itself seal the aperture 102 and provide ingress protection, in addition to or as an alternative to the sealing provided by the adhesive layer 216. The protruding portion 219 of the optical component 212 may be oval in shape as shown, or other shapes.

The adhesive layer 216 may have a shape that is complimentary to the shape of the optical component 212. Each of the adhesive layer 216 and the optical component 212 may be elongated such that the elongate outer ends of the components engage the housing cover 16 and the portion in between, or inner portion, supports the distance sensor 68, 70. In an exemplary embodiment, the optical component 212 and the adhesive layer 216 may both be oval in shape and have a common outer perimeter. Opposite end portions 220, 222 of the adhesive layer 216 are engageable against the housing cover 16 such that the adhesive layer 216 provides the sealing engagement between the housing cover 16 and the distance sensor assembly 200 when the distance sensor assembly 200 is seated in a corresponding tilted seat. For example, the adhesive layer 216 may engage against the surface defining the recessed portion 104 of the housing cover 16 (shown in FIG. 6).

Referring to FIGS. 11 and 12, another adhesive material 224 may be provided between the PCBA 202 and the optical component 212, such as between a PCBA-facing surface 226 of the optical component 212 and the second surface 210 of the PCBA 202. The adhesive material 224 may be a cyanoacrylate material or other acrylate material. Other adhesive materials may be suitable.

As shown in FIG. 14, when the distance sensor assembly 200 is assembled, an air gap 227 may be defined between the distance sensor 68, 70 and the optical component 212. The air gap 227 enables calibration of the distance sensor 68, 70 according to manufacturer specifications. Providing the air gap 227 is also advantageous in providing a clearance for mounting the optical component 212 with the PCBA 202 and over the distance sensor 68, 70 to enclose the distance sensor 68, 70.

In other exemplary embodiments, the distance sensor 68, 70 may be positioned behind the housing cover without the optical component. In still other embodiments, the optical component may be integrally formed with the housing cover as a single monolithic component. The optical component 212 may be integrally formed with the housing base or the housing cover. Other arrangements of the optical component may also be suitable. For example, the optical component may be co-located or located proximate the light-emitting element.

Figure 15:
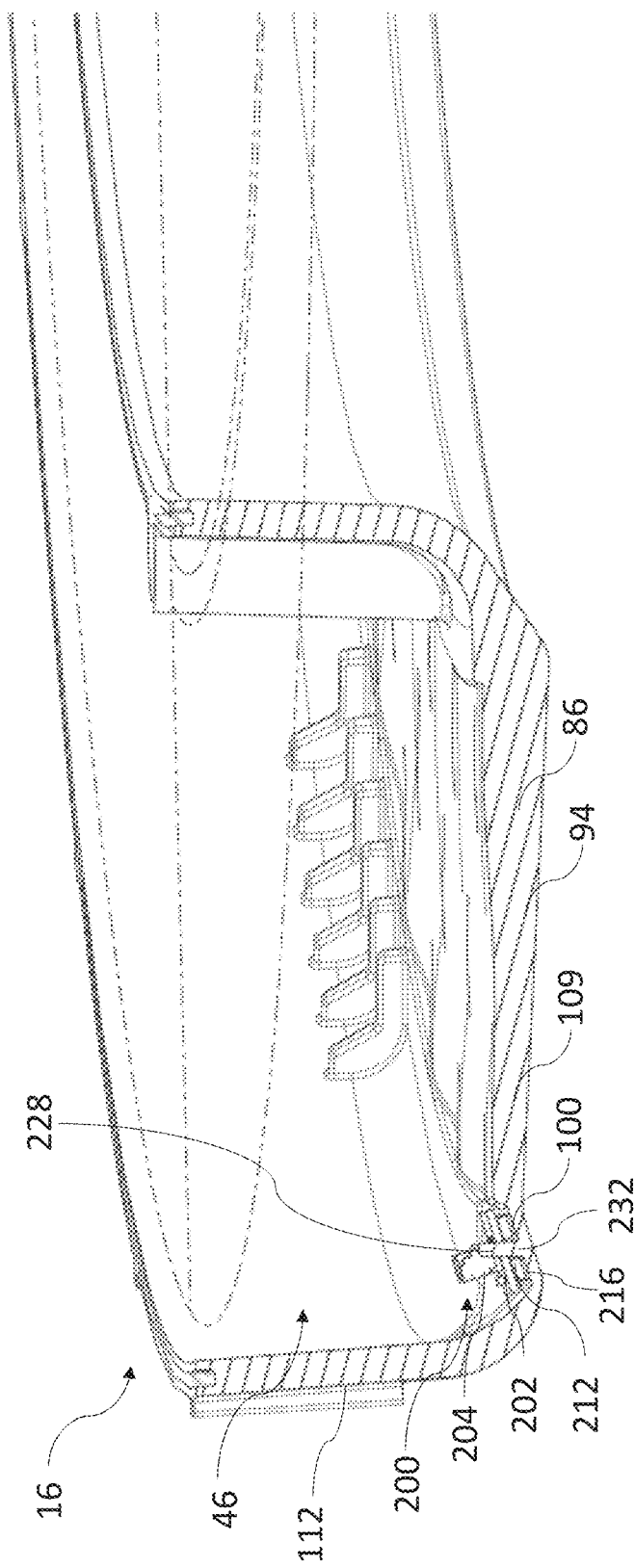
FIG. 15 is a side cross section view of a portion of the light head, showing a locating post, the tilted seat, and the distance sensor assembly.
Figure 16:
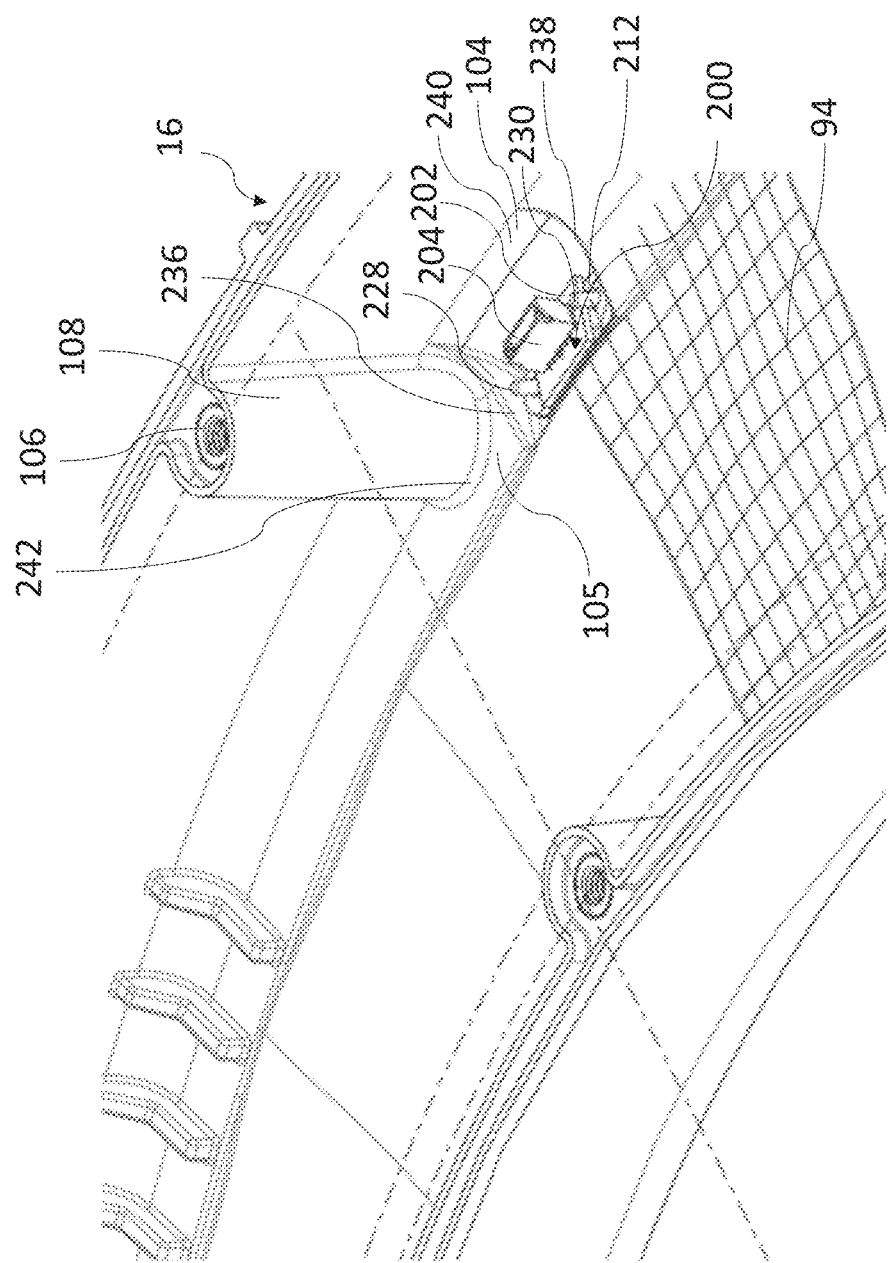
FIG. 16 is a top perspective cross section view of a portion of the light head, showing locating posts and the distance sensor assembly.

Referring in addition to FIGS. 15 and 16, the distance sensor assembly 200 may be mounted to the housing cover 16 using features formed integrally with the housing cover 16, separate attachment mechanisms, or a combination thereof. The bottom wall 109 of the annular shape outer cover 86 may be formed to have a plurality of locating posts 228, 230 that protrude from the housing cover 16 to support the distance sensor assembly 200. The locating posts 228, 230 may be formed on the tilted seats 98, 100 and engageable with a corresponding one of the distance sensor assemblies 200. The locating posts 228, 230 may be molded or formed integrally with the housing cover 16 as a single monolithic structure that extends from the tilted seat 98, 100 of the housing cover 16.

Each locating post 228, 230 may extend upwardly from the bottom wall 109 into the interior cavity 46 of the housing cover 16 such that the locating posts 228, 230 are accommodated inside the housing cover 16. The interior cavity 46 may be formed by the side wall 112 and the bottom wall 109 of the housing cover 16. The direction in which the locating posts 228, 230 extend may be normal or obliquely angled relative to the tilted seat 98, 100. The locating post 228, 230 may have any suitable shape such as a tapered and/or cylindrical shape. The locating posts 228, 230 may be formed radially outwardly relative to the annular shape lens 38 such that the locating posts 228, 230 do not interfere with a rotational path of the annular shape lens 38.

Each distance sensor assembly 200 is formed to have a corresponding locating feature for mounting the distance sensor assembly 200 relative to the locating post 228, 230 such that the locating post 228, 230 limits axial movement of the distance sensor assembly 200 relative to the locating post 228, 230. The engaging portion may be formed as through-holes through which the locating posts 228, 230 extend. Forming the locating posts 228, 230 to be tapered enables the optical component 212 to slide down the locating post 228, 230 thereby aligning the optical component 212, and thus the distance sensor assembly 200, in the x-y plane.

The locating posts 228, 230 may protrude from a corresponding one of the tilted seats 98, 100 and have a tapered shape that tapers in a protrusion direction away from the corresponding one of the tilted seats 98, 100. The locating posts 228, 230 may be tapered radially inwardly in the protruding direction of the locating posts 228, 230 relative to the tilted seat 100. The shape of the locating posts 228, 230 may enable the optical component 212 to have a rocking movement for adjusting the optical component 212 until the optical component 212 is engaged against the tilted seat 98, 100. When assembled, a thicker base portion 232 of the locating post 228 may limit lateral movement of the optical component 212. The tilted seat 100 is formed as an alignment surface that captures the distance sensor assembly 200 in the z-direction and orients the distance sensor assembly 200 rotationally.

As shown in FIGS. 9-14, each end portion of the optical component 212 is formed with through-holes 233 that are configured to receive a corresponding locating post 228, 230. The locating posts 228, 230 may be formed on the tilted seats 98, 100 to be engageable with the optical component 212, for example, by the locating posts 228, 230 extending through the opposite end through-holes 233. The number of apertures formed in the optical component 212 may correspond to the number of locating posts 228, 230. Two locating posts 228, 230 may be suitable. In other embodiments, one or more than two locating posts 228, 230 may be provided. Similarly, the adhesive layer 216 is formed with through-holes 234 that correspond to the through-holes 233 of the optical component 212 and are configured to receive the corresponding locating post 228, 230. Each through-hole 233, 234 may be circular in shape or have a shape that is suitable for receiving the locating post 228, 230. As shown in FIG. 14, the through-holes 234 of the adhesive layer 216 may be formed to have a larger diameter relative to the diameter of the through-holes 233 of the optical component 212 to provide clearance during assembly of the distance sensor assembly 200.

When mounted to the light cover 16, the adhesive layer 216 and the optical component 212 face or mate with the engaging surface of the tilted seat 100 defined by the bottom wall 109 of the annular shape outer cover 86. As shown in FIG. 16, both the adhesive layer 216 and the optical component 212 are retained via the through-holes 233, 234 (shown in FIGS. 9-14) receiving the locating posts 228, 230 therethrough. The PCBA 202 is positioned on the optical component 212 between the locating posts 228, 230 and the electrical interface or plug 204 extends upwardly past the locating posts 228, 230.

As shown in FIG. 16, the locating posts 228, 230 may be formed in the recessed portion 104 of the housing cover 16 that is adjacent the boss 108. The recessed portion 104 may be defined between sidewalls 236, 238 of the outer peripheral surface 105. The sidewalls 236, 238 extend normal to the surface that defines the tilted seat 100 (shown in FIG. 15). A back wall 240 extends axially between the sidewalls 236, 238 and is formed to have a curvature such that the locating posts 228, 230 and the distance sensor assembly 200 are fully accommodated within the recessed portion 104 and do not protrude past a height of the sidewalls 236, 238. The height of the sidewalls 236, 238 may be formed to be lower relative to a bottom 242 of the boss 108 that includes the threaded openings 106 for securing the housing cover 16 and the housing base.

When the distance sensor assemblies 200 are posited relative to the housing cover 16 by the locating posts 228, 230, the locating posts 228, 230 may undergo an ultrasonic heat staking process, whereby the locating posts 228, 230 are deformed to form an interference fit with the distance sensor assembly 200. In this regard, it will be appreciated that the heat staking of the locating posts 228, 230 may be used as an added or alternative means to the adhesive layer 216 for sealing the optical component 212 to the housing cover 16. Other securing methods and devices may be used to mount the distance sensor assembly 200 to the housing cover 16. For example, the distance sensor assembly 200 may be integrated in the housing cover 16 via ultrasonic welding, a threaded connection, or a press-fit connection.

Any suitable manufacturing method may be used to form a light head having any of the features aforementioned. For example, processes such as injection molding, blow molding, thermoforming, transfer molding, reaction injection molding, compression molding, and extrusion, or any combination thereof may be suitable.

Figure 17:
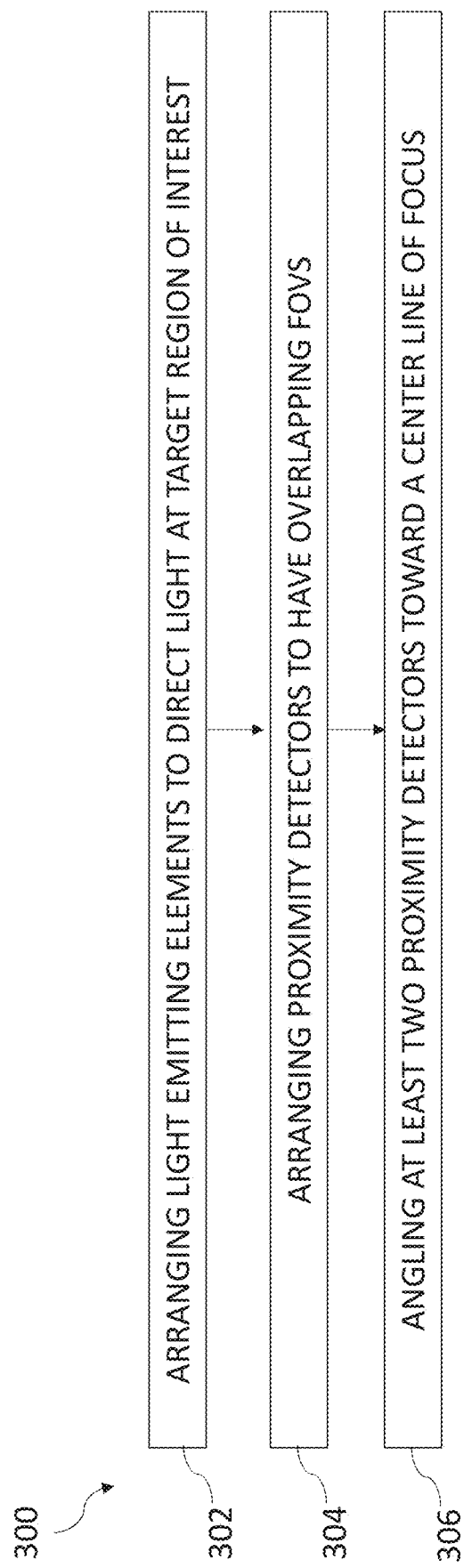
FIG. 17 is a flowchart showing a method of proximity detection for a surgical light.

Referring now to FIG. 17, a flowchart for a method 300 of proximity detecting for a surgical light head is shown. The method 300 may be implemented in a surgical light head, such as the surgical light head 12 of FIG. 1. A first step 302 of the method 300 may include arranging a plurality of light emitting elements 40 in a housing 12 (shown in FIG. 2) to direct light at a target region of interest 72 (shown in FIG. 4). A step 304 of the method 300 may include arranging at least two distance sensors 68, 70 to have field of views 74 that overlap to define a common detection region of interest 75 (shown in FIG. 4). The common detection region of interest 75 at least partially overlaps with the target region of interest 72. A step 304 of the method 300 includes arranging the at least two distance sensors 68, 70 to be obliquely angled toward a center line of focus F of the surgical light head 12 (shown in FIG. 4).

Figure 18:
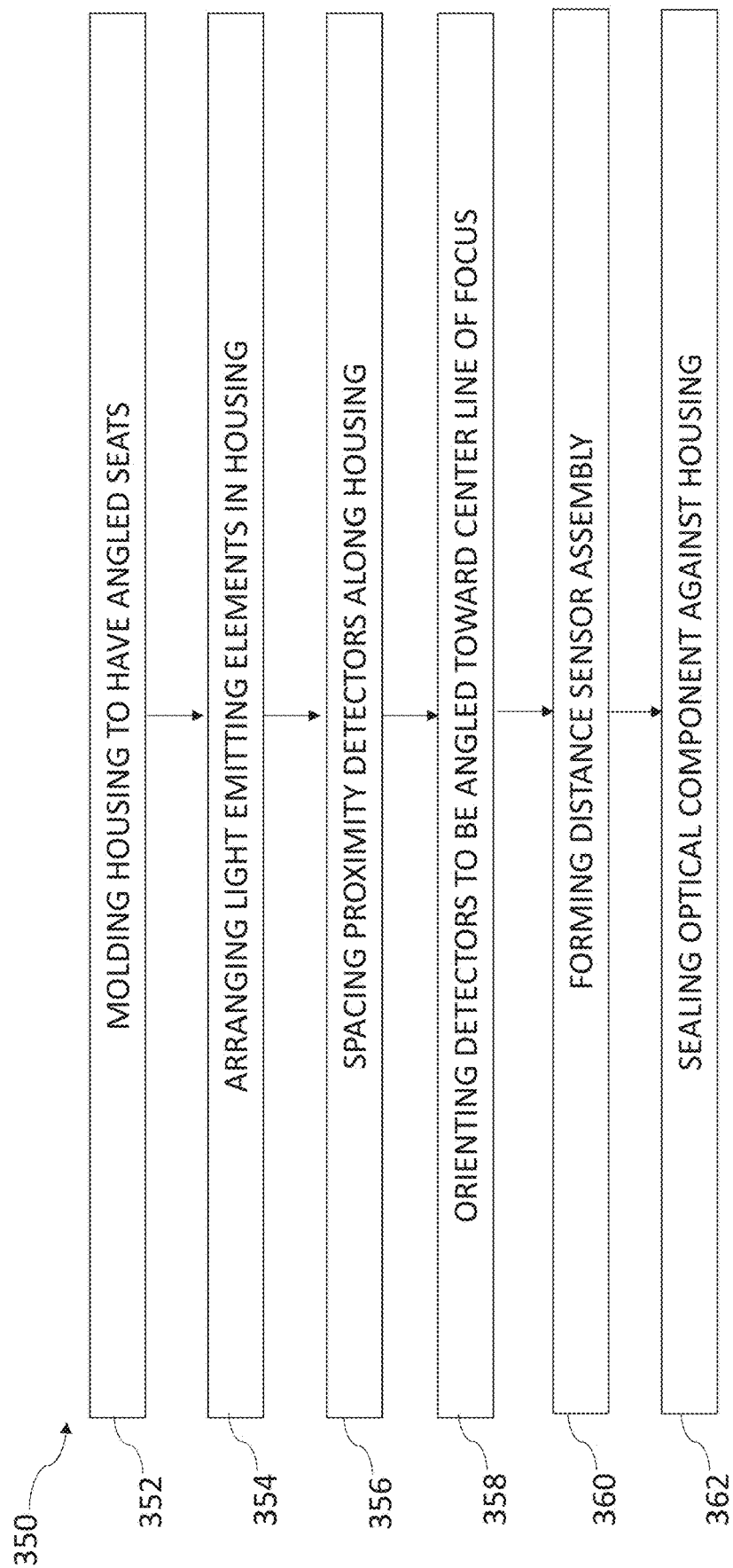
FIG. 18 is a flowchart showing a method of forming a surgical light.

Referring now to FIG. 18, a flowchart for a method 350 of forming a surgical light head, such as the surgical light head 12, is shown. Step 352 of the method 350 includes molding the housing 12 to have a plurality of tilted seats 98, 100 (shown in FIGS. 6-8) as a single monolithic component. Step 352 may include molding locating posts 228, 230 (shown in FIGS. 15 and 16) with the housing 12. Step 354 may include arranging the plurality of light emitting elements 40 in the housing 12 and step 356 of the method 350 includes spacing the plurality of distance sensors 68, 70 along a periphery of the housing 12. Step 358 of the method 350 includes orienting the plurality of distance sensors 68, 70 to be obliquely angled toward the center line of focus F of the surgical light head 12. Step 358 may include arranging the plurality of distance sensors 68, 70 against the plurality of tilted seats 98, 100 to position the plurality of distance sensors 68, 70.

Step 360 of the method 350 includes forming a distance sensor assembly 200 (shown in FIGS. 9-14). Step 360 may include communicatively coupling the housing 12 and one of the plurality of distance sensors 68, 70 with a PCBA 202 and mounting the PCBA 202 to an optical component 212. Mounting the PCBA 202 to the optical component 212 may include covering the distance sensor 68, 70 with the optical component 212 such that the distance sensor 68, 70 is configured to transmit and receive distance sensing signals through the optical component 212. An air gap 227 may be defined between the distance sensor 68, 70 and the optical component 212.

The method 350 may further include a step 362 of sealing the optical component 212 relative to the housing 12. Step 362 may include engaging the optical component 212 with the locating posts 228, 230 to position the distance sensor assembly 200. A heat staking process may be used to secure the optical component 212 and the locating posts 228, 230.

The surgical light head having any combination of the features described herein is advantageous in that the surgical light head has improved proximity detection. Forming the distance sensors to be spaced about the light head and obliquely angled toward the center line of focus ensures accuracy in the detected distance measurements, such that blockage of one sensor will not significantly impede the measurements, such as the voted output measurements, from the other sensors. Integrating the sensors into the light head via the tilted seats and/or the optical component ensures proper aiming of the distance sensors and provides ingress protection for the light head without sacrificing accuracy of the distance sensors.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A surgical light head, comprising:
a housing;
a plurality of light emitting elements arranged in the housing and configured to direct light at a target region of interest; and
a plurality of distance sensors arranged in the housing, wherein the distance sensors are configured to measure a distance to an object and are obliquely angled relative to a center line of focus of the surgical light head, wherein at least two of the distance sensors have field of views that extend outwardly from the corresponding distance sensor, wherein the field of views define respective distance sensor detection regions of interest, and wherein the distance sensor detection regions of interest overlap to define a common detection region of interest, wherein the common detection region of interest at least partially overlaps with the target region of interest.

2. The surgical light head according to claim 1, wherein the plurality of distance sensors are mounted along a periphery of the housing in a spaced relationship relative to each other.

3. The surgical light head according to claim 2, wherein the plurality of distance sensors are evenly spaced.

4. The surgical light head according to claim 1, wherein the plurality of distance sensors are obliquely angled relative to the center line of focus by an angle that is between 0.5 and 20 degrees.

5. The surgical light head according to claim 1, wherein the plurality of distance sensors includes a single inner distance sensor arranged proximate the center line of focus and a plurality of outer distance sensors that are radially spaced relative to the inner distance sensor.

6. The surgical light head according to claim 5, further comprising an annular shape first lens that has a rotation axis, wherein the housing includes a housing cover including a cavity within which the annular shape first lens is rotatable about the rotation axis, wherein the housing cover includes a second lens, and wherein the outer distance sensors are arranged radially outwardly relative to the annular shape first lens and the second lens.

7. The surgical light head according to claim 1, wherein the field of views are defined by cones having an opening angle that is between and 40 degrees.

8. The surgical light head according to claim 1, wherein the plurality of distance sensors includes between five and ten distance sensors that are separate and spaced about the housing.

9. The surgical light head according to claim 1, wherein the plurality of distance sensors are infrared distance sensors.

10. A surgical light head, comprising:
a housing defining a center line of focus of the surgical light head;
a plurality of distance sensors; and
a plurality of tilted seats formed on the housing and configured for supporting the plurality of distance sensors, wherein the plurality of tilted seats are obliquely angled toward the center line of focus such that when the distance sensors are seated against the seats, the distance sensors are obliquely angled toward the center line of focus.

11. The surgical light head according to claim 10, wherein the plurality of tilted seats are molded with the housing as a single monolithic component.

12. The surgical light head according to claim 10, wherein the plurality of tilted seats includes a single inner seat formed proximate the center line of focus and a plurality of outer seats that are formed on a periphery of the housing and radially spaced from the inner seat.

13. The surgical light head according to claim 12, further comprising an annular shape first lens that has a rotation axis, wherein the housing includes a housing cover including a cavity within which the annular shape first lens is rotatable about the rotation axis, wherein the housing cover includes a second lens, and wherein the outer seats are arranged radially outwardly relative to the annular shape first lens and the second lens.

14. The surgical light head according to claim 10, wherein the plurality of tilted seats are obliquely angled relative to the center line of focus by an angle that is between 0.5 and 20 degrees.

15. The surgical light head according to claim 10, further comprising a plurality of distance sensor assemblies that each include a corresponding one of the plurality of distance sensors and a printed circuit board assembly including an electrical interface communicatively coupled between the housing and the corresponding one of the plurality of distance sensors.

16. The surgical light head according to claim 15, wherein each of the plurality of distance sensor assemblies include an optical component that covers the corresponding one of the plurality of distance sensors, the optical component being matingly engageable against a corresponding one of the tilted seats and coupled to the printed circuit board assembly, wherein the corresponding one of the plurality of distance sensors is configured to transmit and receive distance sensing signals through the optical component.

17. The surgical light head according to claim 16, further comprising an adhesive layer disposed between the optical component and the corresponding one of the tilted seats.

18. The surgical light head according to claim 15, further comprising a plurality of locating posts that are formed on the plurality of tilted seats and engageable with a corresponding one of the plurality of distance sensor assemblies.

19. The surgical light head according to claim 18, wherein the plurality of locating posts are integrally formed with the housing as a single monolithic component.

20. The surgical light head according to claim 18, wherein the locating posts protrude from a corresponding one of the plurality of tilted seats and have a tapered shape that tapers in a protrusion direction away from the corresponding one of the plurality of tilted seats.

21. The surgical light head according to claim 10, further comprising a plurality of light emitting elements arranged in the housing and configured to direct light at a target region of interest that defines the center line of focus, wherein the plurality of distance sensors are obliquely angled toward the center line of focus when seated in the tilted seats, whereby at least two of the distance sensors have field of views that overlap to define a common detection region of interest, wherein the common detection region of interest at least partially overlaps with the target region of interest.

22. A surgical light head, comprising:
a housing; and
a plurality of distance sensor assemblies integrated into the housing,
wherein each of the plurality of distance sensor assemblies includes a distance sensor, a printed circuit board assembly having an electrical interface communicatively coupled between the housing and the distance sensor, and an optical component that covers the distance sensor, the optical component being sealed to the housing and coupled to the printed circuit board assembly, and wherein the distance sensor is configured to transmit and receive distance sensing signals through the optical component.

23. The surgical light head according to claim 22, further comprising an adhesive layer disposed between the optical component and the housing.

24. The surgical light head according to claim 22, wherein the printed circuit board assembly and the optical component are adhered by an acrylate adhesive material.

25. The surgical light head according to claim 22, wherein the corresponding one of the plurality of distance sensors and the optical component define an air gap therebetween.

26. The surgical light head according to claim 22, wherein the housing defines a plurality of tilted seats configured for supporting the plurality of distance sensor assemblies, the tilted seats being obliquely angled toward a center line of focus of the surgical light head.

27. The surgical light head according to claim 26, further comprising a plurality of locating posts formed on the tilted seats that are engageable with the optical component.

28. The surgical light head according to claim 22, further comprising a plurality of light emitting elements arranged in the housing and configured to direct light at a target region of interest, wherein at least two of the distance sensor assemblies have field of views that overlap to define a common detection region of interest, wherein the common detection region of interest at least partially overlaps with the target region of interest.

29. The surgical light head according to claim 22, wherein the plurality of distance sensor assemblies are obliquely angled relative to a center line of focus of the surgical light head.

30. The surgical light head according to claim 29, wherein the plurality of distance sensor assemblies are obliquely angled relative to the center line of focus by an angle that is between 0.5 and 20 degrees.

31. A method of proximity detecting for a surgical light head, comprising:

arranging a plurality of light emitting elements in a housing to direct light at a target region of interest; and arranging at least two distance sensors that are configured to measure distance to an object to be obliquely angled relative to a center line of focus of the surgical light head and to have field of views that extend outwardly from the corresponding distance sensor, wherein the field of views define respective distance sensor detection regions of interest, and wherein the distance sensor detection regions of interest overlap to define a common detection region of interest, wherein the common detection region of interest at least partially overlaps with the target region of interest.

32. A method of forming a surgical light head, comprising:

arranging a plurality of light emitting elements in a housing;

spacing a plurality of tilted seats and distance sensors along a periphery of the housing;

orienting the tilted seats to be obliquely angle toward a center line of focus of the light head; and arranging the plurality of distance sensors against the plurality of tilted seats to orient the plurality of distance sensors to be obliquely angled toward the center line of focus of the surgical light head.

* * * * *